(12) United States Patent
Min et al.

(10) Patent No.: US 8,946,431 B2
(45) Date of Patent: Feb. 3, 2015

(54) 2-(SUBSTITUTED ETHYNYL)QUINOLINE DERIVATIVES AS MGLUR5 ANTAGONISTS

(71) Applicant: Korea Institute of Science and Technology, Seoul (KR)

(72) Inventors: Sun Joon Min, Seoul (KR); Yong Seo Cho, Seoul (KR); Ae Nim Pae, Seoul (KR); Eun Jeong Lim, Seoul (KR); Ji Yeong Kim, Yangsan-si (KR); Myung Hee Son, Namyangju-si (KR); Jae Kyun Lee, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 13/943,019

(22) Filed: Jul. 16, 2013

(65) Prior Publication Data

US 2014/0206876 A1      Jul. 24, 2014

(30) Foreign Application Priority Data

Jan. 23, 2013   (KR) .......................... 10-2013-0007540

(51) Int. Cl.
| | | |
|---|---|---|
| C07D 215/06 | (2006.01) | |
| A61K 31/04 | (2006.01) | |
| C07D 215/20 | (2006.01) | |
| C07D 401/06 | (2006.01) | |

(52) U.S. Cl.
CPC ............ C07D 215/06 (2013.01); C07D 215/20 (2013.01); C07D 401/06 (2013.01)
USPC ........... 546/176; 546/153; 544/333; 514/312; 514/314; 514/256

(58) Field of Classification Search
CPC .. C07D 215/12; C07D 233/96; C07D 233/64; A61K 31/4709; A61K 31/497
USPC ................. 514/314, 312, 256; 546/176, 153; 544/333
See application file for complete search history.

(56) References Cited

PUBLICATIONS

Araki, Org Biomol Chem, vol. 9, pp. 78-80, 2011.*
F. Gasparini et al., "2-Methyl-6-(phenylethynyl)-pyridine (MPEP), a potent, selective and systemically active mGlu5 receptor antagonist," *Neuropharmacology*, No. 38, 1999, pp. 1493-1503.
Micheli F., "Methylphenylethynylpyridine (MPEP) Novartis," *Curr. Opin. Investig. Drugs*, No. 3, Nov. 2000, pp. 355 (abstract).
B. Schulz et al., "The metabotropic glutamate receptor antagonist 2-methyl-6-(phenylethynyl)-pyridine (MPEP) blocks fear conditioning in rats," *Neuropharmacology*, No. 41, 2001, pp. 1-7.
V. Mutel, "Therapeutic potential of non-competitive, subtype-selective metabotropic glutamate receptor ligands," *Expert Opin. Ther. Patents*, No. 12, 2002, pp. 1845-1852.
T. M. Ballard et al., "The effect of the mGlu5 receptor antagonist MPEP in rodent tests of anxiety and cognition: a comparison," *Psychopharmacology*, No. 179, Mar. 2005, pp. 218-229.
C. Z. Zhu et al., Role of central and peripheral mGluR5 receptors in post-operative pain in rats, *Pain*, No. 114, 2005, pp. 195-202.
M. F. Olive, "Metabotropic Glutamate Receptor Ligands as Potential Therapeutics for Addiction," *Current Drug Abuse Reviews*, No. 2, 2009, pp. 83-98.
C. Keywood et al, "A proof-of-concept study evaluating the effect of ADX10059, a metabotropic glutamate receptor-5 negative allosteric modulator, on acid exposure and symptoms in gastro-oesophageal reflux disease," *Gut*, No. 58, 2009, pp. 1192-1199.
M.-H. Son et al., "Synthesis and biological evaluation of 2-(arylethynyl)quinoline derivatives as mGluR5 antagonists for the treatment of neuropathic pain," *Bioorg. & Med. Chem. Lett.*, 2013, pp. 1-5.

* cited by examiner

*Primary Examiner* — D M Seaman
(74) *Attorney, Agent, or Firm* — Staas & Halsey LLP

(57) ABSTRACT

Provided is a 2-(substituted ethynyl)quinoline derivative having an mGluR5 antagonistic activity and pharmaceutically acceptable salts thereof. The compound of the present invention can be useful as a medicament for treating and preventing mGluR5 receptor-mediated diseases such as Alzheimer's disease, senile dementia, Parkinson's disease, L-DOPA-induced dyskinesia, Huntington's chorea, amyotrophic lateral sclerosis, multiple sclerosis, schizophrenia, anxiety disorder, depression, neuropathic pain, drug dependence, fragile X syndrome, autism, migraine and gastroesophageal reflux disease (GERD).

4 Claims, 1 Drawing Sheet

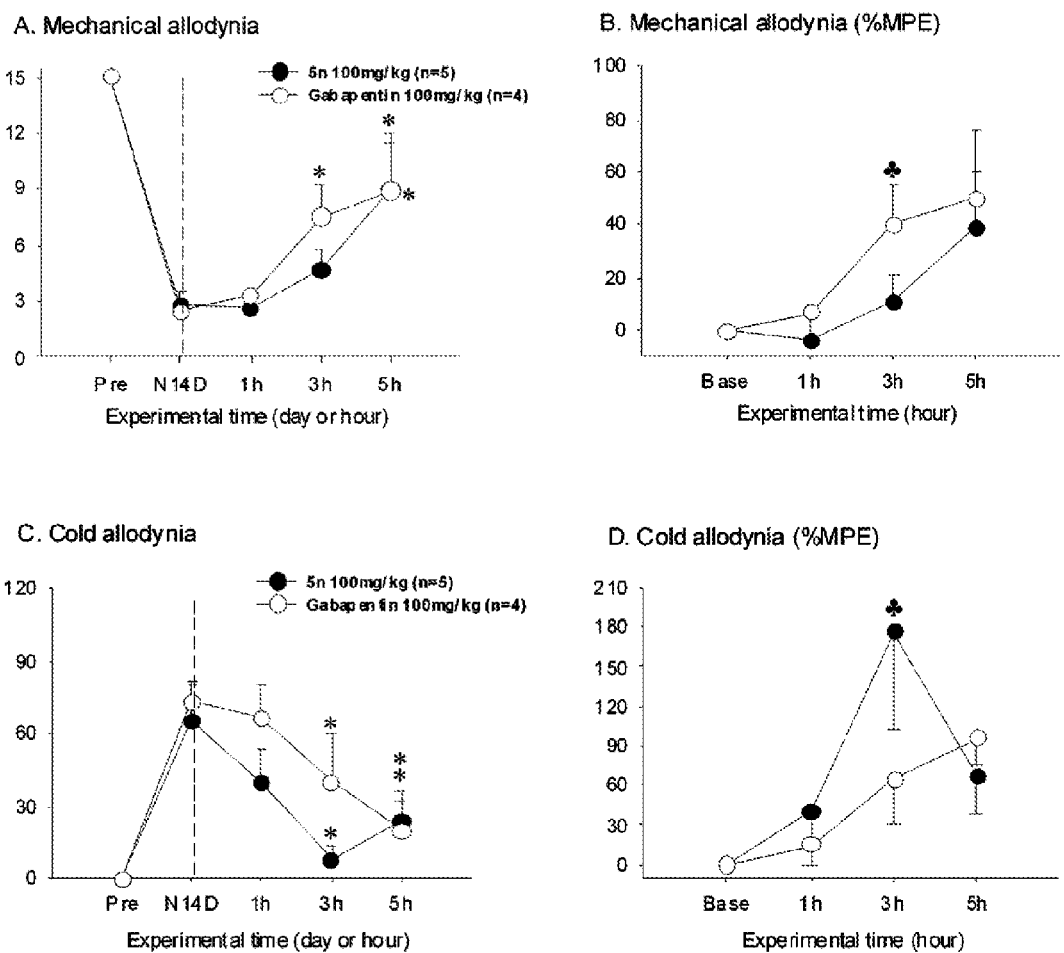

2-(SUBSTITUTED ETHYNYL)QUINOLINE DERIVATIVES AS MGLUR5 ANTAGONISTS

CROSS-REFERENCE TO RELATED APPLICATION

This application claims under 35 U.S.C. §119(a) the benefit of Korean Patent Application No. 10-2013-0007540 filed Jan. 23, 2013, the entire contents of which are incorporated herein by reference.

BACKGROUND (a) Technical Field

The present invention relates to a 2-(substituted ethynyl) quinoline derivative having an mGluR5 antagonistic activity and pharmaceutically acceptable salts thereof. The compound of the present invention can be useful as a medicament for treating and preventing mGluR5 receptor-mediated diseases such as Alzheimer's disease, senile dementia, Parkinson's disease, L-DOPA-induced dyskinesia, Huntington's chorea, amyotrophic lateral sclerosis, multiple sclerosis, schizophrenia, anxiety disorder, depression, neuropathic pain, drug dependence, fragile X syndrome, autism, migraine and gastroesophageal reflux disease (GERD).

(b) Background Art

Glutamate is a most important neurotransmitter in the human body, and divided into two groups of ionotropic receptor (iGluRs) and metabotropic receptor (mGluRs). iGluR refers to a ligand-gated ion channel. In particular, it may be divided into (S)-2-amino-3-(3-hydroxy-5-methyl-4-isoxazolyl)propionic acid (AMPA), N-methyl-D-acpartic acid (NMDA), and Kainate depending on the type of receptor-ligand interactions. mGluR is one of G-protein coupled receptors (GPCR), which may be divided into Groups I, II and III depending on its physiological characteristics. Group I is composed of mGluR1 and mGluR5, acts as a postsynaptic receptor which is involved in the enhancement of neuronal excitation, and activates PLC (phospholipase C) through Gq protein. Group II (mGluR2 and mGluR3) and Group III (mGluR4, mGluR6, mGluR7 and mGluR8) belong to a pretsynaptic receptor, and inhibit the activity of an adeninyl cyclic enzyme system activated through Gi protein.

mGluR5 is predominantly expressed in the hippocampus and cerebral cortex, mainly distributed in the postsynaptic membrane of neurons, and functions to regulate synaptic plasticity. It has been found that mGluR5 is immediately correlated with nervous diseases including fragile X syndrome, pain and drug addict (*Pain* 2005, 114, 195; *Neuropharmacology* 1999, 38, 1493; *Neuropharmacology* 2001, 41, 1; *Curr. Drug Abuse Rev.* 2009, 2, 83). The mGluR5-related diseases can be exemplified by degenerative nervous diseases such as Alzheimer's disease, senile dementia, Parkinson's disease, Huntington's chorea, amyotrophic lateral sclerosis and multiple sclerosis; mental illnesses such as schizophrenia and anxiety; depression, pain and drug dependence (*Expert Opin. Ther.* Patents (2002), 12(12)).

There has been an extensive effort to develop an mGluR5 antagonist. As a result, it has been found that 2-methyl-6-(phenylethynyl)pyridine (MPEP) shows a selective activity as an mGluR5 negative allosteric modulator and is effective for pain, anxiety disorder or depression. However, its pharmacokinetic profile was found to be very poor in clinical trials (*Curr Opin. Invest. Dr.* 2001, 1, 355; *Psychopharmacology* 2005, 179, 218). Further, it has been reported that ADX10059 (Gut. 2009, 58, 1192), which is developed as an mGluR5 antagonist having an alkyne moiety, is effective for fragile X syndrome, gastroesophageal reflux disease (GERD) or migraine. Patients with fragile X syndrome suffer from cognitive disorder, autistic spectrum disorder, aggressiveness, attack, anxiety, compulsive behavior disorder, excessive tactile sensitivity, diarrhea and excessive sensory sensitivity. A selective mGluR5 antagonist can be effectively used for treating fragile X syndrome, depression, Parkinson's disease or L-DOPA-induced dyskinesia. Therefore, there is still a need to develop a novel mGluR5 antagonist with improved selective activity.

The above information disclosed in this Background section is only for enhancement of understanding of the background of the invention and therefore it may contain information that does not form the prior art that is already known in this country to a person of ordinary skill in the art.

SUMMARY OF THE DISCLOSURE

The present invention has been made in an effort to solve the above-described problems associated with prior art.

In one aspect, the present invention provides a novel compound selected from 2-(substituted ethynyl)quinoline derivatives and pharmaceutically acceptable salts thereof.

In another aspect, the present invention provides a pharmaceutical composition for preventing and treating mGluR5 receptor-mediated diseases, which comprises the above novel compound as an active ingredient.

In still another aspect, the present invention provides a method for preparing the above novel compound.

In an exemplary embodiment, the present invention relates to a 2-(substituted ethynyl)quinoline derivative having an mGluR5 antagonistic activity which is represented by the following Formula 1 or pharmaceutically acceptable salts thereof:

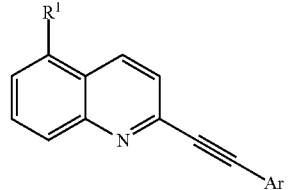

[Formula 1]

wherein Ar is an aryl or a heteroaryl group selected from the group consisting of phenyl, pyridinyl and pyrimidinyl, the aryl or heteroaryl group being substituted or unsubstituted with one to three substituents selected from the group consisting of halo, cyano, $C_1$-$C_{10}$ alkyl, $C_1$-$C_{10}$ haloalkyl and $C_1$-$C_{10}$ alkoxy; and $R^1$ is a hydrogen atom, a halogen atom, a hydroxyl group, $C_1$-$C_{10}$ alkyl, $C_1$-$C_{10}$ alkoxy, or $C_1$-$C_{10}$ alkyl carbonate.

Other aspects and exemplary embodiments of the invention are discussed infra.

BRIEF DESCRIPTION OF THE DRAWINGS

The above and other features of the present invention will now be described in detail with reference to certain exemplary embodiments thereof illustrated the accompanying drawings which are given hereinbelow by way of illustration only, and thus are not limitative of the present invention, and wherein:

FIG. 1 is a graph comparing inhibitory effects on mechanical and cold allodynia when the inventive compound and a control group (gabapentin) were orally administered to SNL neuropathic pain models, respectively.

It should be understood that the appended drawings are not necessarily to scale, presenting a somewhat simplified representation of various exemplary features illustrative of the basic principles of the invention. The specific design features of the present invention as disclosed herein, including, for example, specific dimensions, orientations, locations, and shapes will be determined in part by the particular intended application and use environment.

In the figures, reference numbers refer to the same or equivalent parts of the present invention throughout the several figures of the drawing.

DETAILED DESCRIPTION

Hereinafter reference will now be made in detail to various embodiments of the present invention, examples of which are illustrated in the accompanying drawings and described below. While the invention will be described in conjunction with exemplary embodiments, it will be understood that present description is not intended to limit the invention to those exemplary embodiments. On the contrary, the invention is intended to cover not only the exemplary embodiments, but also various alternatives, modifications, equivalents and other embodiments, which may be included within the spirit and scope of the invention as defined by the appended claims.

Pharmaceutically acceptable salts of the compound represented by Formula 1 according to the present invention can be prepared by conventional methods well-known in the art. The pharmaceutically acceptable salts should have extremely low toxicity to the human body and not adversely affect on biological, physical and chemical properties of the parent compound. The pharmaceutically acceptable salts may include acid-addition salts of pharmaceutically acceptable free acids and a base compound of Formula 1, alkali-metal salts (e.g., sodium salts) and alkali-earth metal salts (e.g., potassium salts), base-addition salts of organic salts and a carboxylic acid of Formula 1, and amino acid-addition salts. The free acids suitable for the preparation of pharmaceutically acceptable salts can be divided into inorganic acids and organic acids. The inorganic acids may include hydrochloric acid, sulfuric acid, nitric acid, phosphoric acid, perchloric acid, bromic acid and the like. The organic acids may include acetic acid, methanesulfonic acid, ethanesulfonic acid, p-toluenesulfonic acid, fumaric acid, maleic acid, malonic acid, phthalic acid, succinic acid, lactic acid, citrate, citric acid, gluconic acid, tartaric acid, salicylic acid, malic acid, oxalic acid, benzoic acid, embonic acid, aspartic acid, glutamic acid and the like. The organic bases suitable for the preparation of organic base-addition salts may include tris(hydroxymethyl) methylamine, dicyclohexylamine and the like. The amino acids suitable for the preparation of amino acid-addition bases may include natural amino acids such as alanin and glycine.

The compound represented by Formula 1 according to the present invention may include all kinds of solvates and hydrates thereof as well as the above pharmaceutically acceptable salts. The pharmaceutically acceptable salts can be prepared according to the conventional method as described below. After the base compound represented by Formula 1 is dissolved in a water-miscible solvent such as methanol, ethanol, acetone or 1,4-dioxane, a free acid or a free base is added thereto, and the resulting mixture is subjected to crystallization or re-crystallization.

In addition, the compound represented by Formula 1 according to the present invention may contain more than one asymmetric (chiral) centers, and thus such a compound may occur in enathimers or diasteromers. Therefore, the present invention includes these isomers alone or in an admixture thereof. Different types of isomers can be separated or decomposed according to conventional methods well-known in the art, or a certain isomer can be prepared according to conventional synthetic methods, or sterospecific or asymmetric synthetic methods.

Further, the present invention includes radioactive derivatives of the compound represented by Formula 1, and such radioactive compounds can be effectively used in in vivo studies.

Hereinafter, substitutents used for the definition of the compound according to the present invention are explained in detail.

The term 'halogen atom' as used herein refers to chloro, fluoro, bromo or iodo.

The term 'alkyl' as used herein refers to $C_1$-$C_{10}$ aliphatic saturated hydrocarbon groups such as methyl, ethyl, n-propyl, i-propyl, n-butyl, i-butyl, t-butyl, n-pentyl, i-pentyl, neopentyl, t-pentyl, n-hexyl, i-hexyl, heptyl, octyl and so on.

The term 'haloalkyl' as used herein refers to alkyl groups whose hydrogen atom is substituted with one or more halgen atoms such as trifluormethyl.

The term 'alkoxy' as used herein refers to hydroxyl groups whose hydrogen atom is substituted with one selected from $C_1$-$C_{10}$ alkyl groups including methoxy, ethoxy, n-propoxy, i-propoxy, n-butoxy, i-butoxy, t-butoxy and so on.

The term 'aryl' as used herein refers to $C_6$-$C_{15}$ aromatic hydrocarbon groups having one to three ring (mono-, bi-, or tricyclic) moieties such as phenyl, naphthyl, anthranyl, phenanthrenyl and the like. The aryl group suitable for the present invention is a phenyl group, and the phenyl group can be unsubstituted or substituted with one to three substituents selected from halo, cyano, $C_1$-$C_{10}$ alkyl, $C_1$-$C_{10}$ haloalkyl and $C_1$-$C_{10}$ alkoxy.

The term 'heteroaryl' as used herein may include pyrrolyl, puranyl, thiophenyl, pyrazolyl, imidazolyl, oxazolyl, isoxazolyl, thiazolyl, isothiazolyl, triazolyl, oxadiazolyl, thiadiazolyl, tetrazolyl, pyridinyl, pyrazinyl, pyridazinyl, pyrimidinyl, triazolyl, indolyl, isoindolyl, benzofuranyl, benzofurazinyl, dibenzofuranyl, isobenzofuranyl, indazolyl, benzimidazolyl, benzoxazolyl, benzisoxazolyl, benzothiazolyl, dibenzothiophenyl, naphtyrinyl, benzisothiazolyl, quinolinyl, isoquinolinyl, quinoxalinyl, phthalazinyl, chinolinyl, quinazolinyl and the like, and refers to aromatic heterohydrocarbon groups having one or more heteroatoms selected from nitrogen, oxygen and sulfur. The heterohydrocarbon groups may contain one to three (mono-, bi-, or tricyclic) pentagonal, hexagonal or heptagonal ring moieties. Preferably, the heteroaryl group refers to pyridinyl or pyrimidinyl, more preferably pyridine-2-yl, pyridine-3-yl, pyridine-2-yl, pyrimidine-2-yl, pyrimidine-4-yl, or pyrimidine-5-yl. The heteroaryl group can be unsubstituted or substituted with one to three substituents selected from the group consisting of halo, cyano, $C_1$-$C_{10}$ alkyl, $C_1$-$C_{10}$ haloalkyl and $C_1$-$C_{10}$ alkoxy.

Representative examples of the compound of Formula 1 according to the present invention are as follows:
2-(phenylethynyl)quinoline;
5-methoxy-2-(phenylethynyl)quinoline;
2-(phenylethynyl)quinoline-5-ylpivalate;
2-(phenylethynyl)quinoline-5-ol;
5-chloro-2-(phenylethynyl)quinoline;
5-bromo-2-(phenylethynyl)quinoline;
2-(pyridine-3-ylethynyl)quinoline;
5-methoxy-2-(pyridine-3-ylethynyl)quinoline;

5-ethoxy-2-(pyridine-3-ylethynyl)quinoline;
2-(pyridine-3-ylethynyl)quinoline-5-ylpivalate;
2-(pyridine-3-ylethynyl)quinoline-5-ol;
5-chloro-2-(pyridine-3-ylethynyl)quinoline;

Meanwhile, the present invention provides a method for preparing a 2-(substituted ethynyl)quinoline derivative represented by Formula 1, which can be illustrated by following Reaction Formula 1.

[Reaction Formula 1]

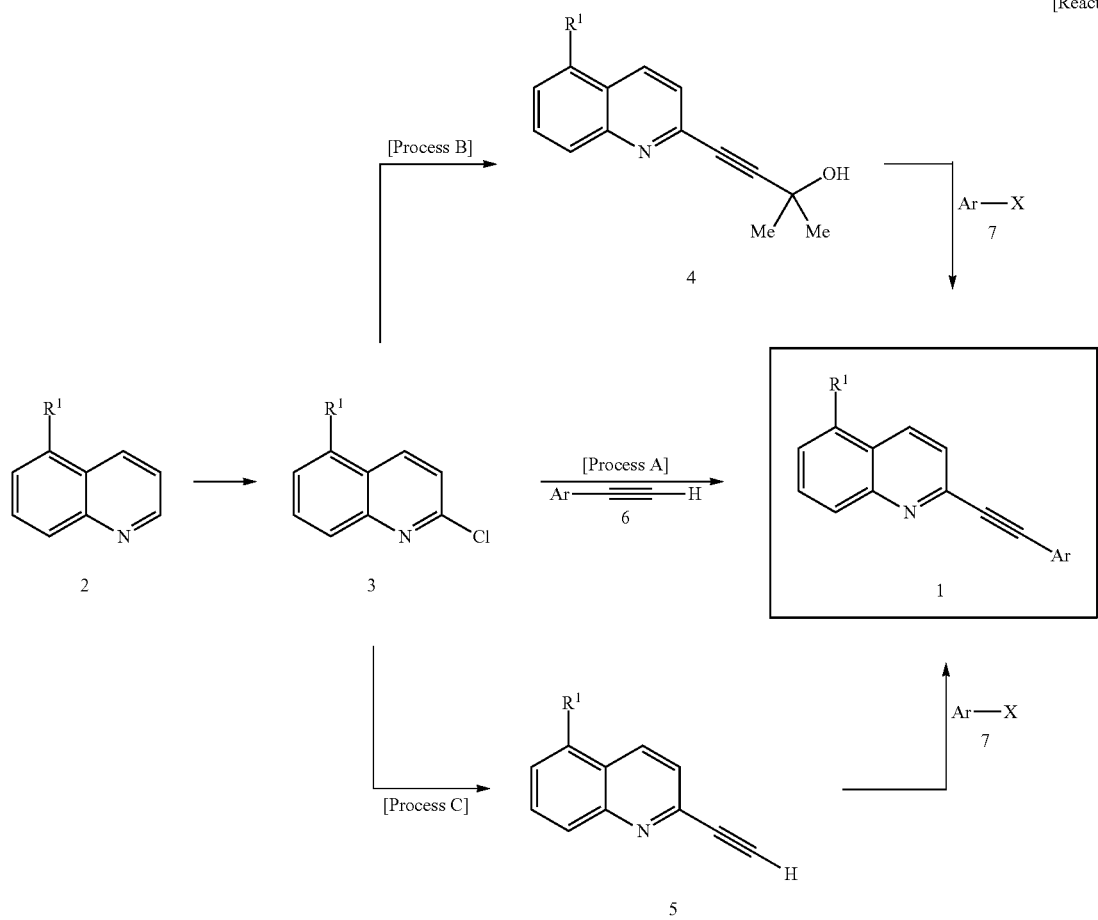

5-bromo-2-(pyridine-3-ylethynyl)quinoline;
2-(pyridine-2-ylethynyl)quinoline;
2-(pyridine-2-ylethynyl)quinoline-5-ylpivalate;
2-(pyridine-2-ylethynyl)quinoline-5-ol;
5-chloro-2-(pyridine-2-ylethynyl)quinoline;
5-bromo-2-(pyridine-2-ylethynyl)quinoline;
2-((3-(trifluoromethyl)pyridine-2-yl)ethynyl)quinoline;
2-((3-fluoropyridine-2-yl)ethynyl)quinoline;
2-((3-methylpyridine-2-yl)ethynyl)quinoline;
2-((4-(trifluoromethyl)pyridine-2-yl)ethynyl)quinoline;
2-(quinoline-2-ylethynyl)isonicotinonitrile;
2-((4-methylpyridine-2-yl)ethynyl)quinoline;
2-((5-(trifluoromethyl)pyridine-2-yl)ethynyl)quinoline;
2-((5-fluoropyridine-2-yl)ethynyl)quinoline;
2-((5-methylpyridine-2-yl)ethynyl)quinoline;
2-((6-(trifluoromethyl)pyridine-2-yl)ethynyl)quinoline;
6-(quinoline-2-ylethynyl)picolinonitrile;
2-((6-fluoropyridine-2-yl)ethynyl)quinoline;
2-((6-methoxypyridine-2-yl)ethynyl)quinoline;
2-(pyrimidine-2-ylethynyl)quinoline;
2-((4-(trifluoromethyl)pyrimidine-2-yl)ethynyl)quinoline;
2-((5-fluoropyrimidine-2-yl)ethynyl)quinoline;
2-(pyrimidine-5-ylethynyl)quinoline.

Process A; Process B; Process C
(wherein Ar and $R^1$ are the same as defined in Formula 1, X represents a halogen atom.)

Hereinafter, each step of the preparation method according to Reaction Formula 1 can be explained in detail.

First, a quinoline compound represented by Formula 2 is reacted with chlorine, to thereby obtain a quinoline-2-yl chloride compound represented by Formula 3. The above chlorination reaction can be conducted under the presence of meta-chloroperbenzoic acid (mCPBA) and phosphorous oxychloride ($POCl_3$) and at a temperature ranging from −20° C. to a reflux temperature of a solvent used. There is no limitation to the type of reaction solvents so long as they are conventional organic solvents having no influence on the reaction, and a representative example thereof is dichloromethane.

Next, a 2-(substituted ethynyl)quinoline derivative represented by Formula 1 as a target compound can be prepared from the quinoline-2-yl chloride compound represented by Formula 3. According to the method of the present invention, the target compound can be prepared by one of three processes (A to C) as described in Reaction Formula 1.

In Process A, the quinoline-2-yl chloride compound represented by Formula 3 is directly subjected to a coupling reaction with an aryl acetylene compound represented by Formula 6, to thereby prepare the target compound represented by Formula 1. The above coupling reaction can be carried out under the presence of PdCl$_2$ (PPh$_3$)$_2$, copper iodide (CuI), and a base. The base suitable for the reaction can be conventional organic bases or inorganic bases well-known in the art, and representative examples thereof can include the organic bases such as triethylamine, diisopropylamine and pyridine and the inorganic bases such as sodium hydroxide and potassium hydroxide. This reaction can be conducted under heating, and the resulting mixture can be heated to a reflux temperature of a solvent used. There is no limitation to the type of reaction solvents so long as they are conventional organic solvents having no influence on the reaction, and a representative example thereof is tetrahydrofuran (THF).

In Process B, the quinoline-2-yl chloride compound represented by Formula 3 is directly subjected to a coupling reaction with 2-methyl-3-butyn-2-ol, to thereby synthesize 2-methyl-4-(quinoline-2-yl)but-3-yn-2-ol represented by Formula 4. The thus synthesized 2-methyl-4-(quinoline-2-yl)but-3-yn-2-ol represented by Formula 4 is then subjected to a substitution reaction with aryl halide represented by Formula 7, to thereby prepare the target compound represented by Formula 1. Each of the above coupling and substitution reactions can be performed under the presence of PdCl$_2$(PPh$_3$)$_2$, copper iodide (CuI), and a base. The base suitable for the reaction can be conventional organic bases or inorganic bases well-known in the art, and representative examples thereof can include the organic bases such as triethylamine, diisopropylamine and pyridine and the inorganic bases such as sodium hydroxide and potassium hydroxide. These reactions can be conducted under heating, and the resulting mixture can be heated to a reflux temperature of a solvent used. There is no limitation to the type of reaction solvents so long as they are conventional organic solvents having no influence on the reaction. Also, these reactions can be conducted under solvent-free condition.

In Process C, the quinoline-2-yl chloride compound represented by Formula 3 is subjected to a coupling reaction with trimethylsilyl acetylene, followed by removing a trimethylsilyl (TMS) protecting group therefrom, to thereby prepare 2-ethynylquinoline represented by Formula 5. The thus prepared 2-ethynylquinoline represented by Formula 5 is subjected to a substitution reaction with aryl halide represented by Formula 7, to thereby prepare the target compound represented by Formula 1. Each of the above coupling and substitution reactions can be performed under the presence of PdCl$_2$(PPh$_3$)$_2$, copper iodide (CuI), and a base. The base suitable for the reaction can be conventional organic bases or inorganic bases well-known in the art, and representative examples thereof can include the organic bases such as triethylamine, diisopropylamine and pyridine and the inorganic bases such as sodium hydroxide and potassium hydroxide. These reactions can be conducted under heating, and the resulting mixture can be heated to a reflux temperature of a solvent used. There is no limitation to the type of reaction solvents so long as they are conventional organic solvents having no influence on the reaction. Also, these reactions can be conducted under solvent-free condition.

Meanwhile, the present invention includes a pharmaceutical composition comprising the compound represented by Formula 1, pharmaceutically acceptable salts, solvates or hydrates thereof as an active ingredient.

Since the compound of Formula 1 according to the present invention shows excellent inhibitory activity on mGluR5, it can be used as a medicament for preventing or treating mGluR5 receptor-mediated diseases. The mGluR5 receptor-mediated diseases according to the present invention may include Alzheimer's disease, senile dementia, Parkinson's disease, L-DOPA-induced dyskinesia, Huntington's chorea, amyotrophic lateral sclerosis, multiple sclerosis, schizophrenia, anxiety disorder, depression, neuropathic pain, drug dependence, fragile X syndrome, autism, migraine, gastroesophageal reflux disease (GERD) and the like, but are not limited thereto.

The pharmaceutical composition of the present invention can comprise the compound represented by Formula 1, pharmaceutically acceptable salts, solvates or hydrates thereof as an active ingredient, and further comprise pharmaceutically acceptable carriers, adjuvants and excipients that are conventionally non-toxic. The pharmaceutical composition of the present invention can be formulated into a variety of dosage forms, for example, formulations for oral administration such as tablets, capsules, troches, solutions or suspensions, or formulations for parenteral administration.

The excipients suitable for the pharmaceutical composition of the present invention may include a sweetening agent, a binder, a dissolving agent, a solubilizing agent, a wetting agent, an emulsifying agent, a buffering agent, an adsorbent, a disintegrator, an anti-oxidant, a preservative, a lubricant, a filler, a flavoring agent and the like, but are not limited thereto. For example, these excipients may include lactose, dextrose, sucrose, mannitol, sorbitol, cellulose, glycine, silica, talc, stearic acid, sterine, magnesium stearate, magnesium aluminum silicate, starch, gelatin, tragacanth gum, alginic acid, sodium alginate, methylcellulose, sodium carboxyl methylcellulose, agar, water, ethanol, polyethylene glycol, polyvinyl pyrrolidone, sodium chloride, potassium chloride, orange essence, strawberry essence, vanilla fragrance and the like.

Further, the administration frequency and dose of the compound of the present invention can be determined by several related factors including the types of diseases to be treated, administration routes, the patients age, gender, weight and severity of the illness. For example, based on an adult patient having a weight of 70 kg, the compound of the present invention can be administered at a dose of 0.01 to 1,000 mg/day. The dose can be administered in single or divided into several times per day depending on the judgment of a physician or a pharmacist.

A better understanding of the present invention may be obtained through the following Examples, Formulation Examples, and Experimental Examples which are set forth to illustrate, but are not to be construed as the limits of the present invention.

EXAMPLES

The following examples illustrate the invention and are not intended to limit the same.

Example

Synthesis of 2-(substituted ethynyl)quinoline derivative

Example 1

2-Chloro-5-methoxyquinoline

After 5-methoxyquinoline (104.3 mg, 0.655 mmol) was dissolved in dichloromethane (3 mL), meta-chloroperbenzoic acid (mCPBA; 195 mg, 1.13 mmol) was added thereto at 0° C., and the resulting mixture was stirred for 30 min. After the stirring for 30 min, the reaction temperature was increased from 0° C. to room temperature, followed by further stirring for 3 hr. The completion of the reaction was confirmed by TLC (EtOAc/MC/Hexane=1:2:4). When the reaction was completed, the reaction mixture was extracted with an aqueous solution of 4 N NaOH and dichloromethane, to thereby separate an organic layer. The organic layer was dried over anhydrous $MgSO_4$ and filtered. The resulting filtrate was concentrated under reduced pressure, to thereby generate a white solid. The thus generated solid was dissolved in dichloromethane (2.5 mL) and added with phosphorous oxychloride ($POCl_3$; 0.09 mL, 0.992 mmol). The resulting mixture was subjected to distillation under reflux at 60° C. for 3 hr. The completion of the reaction was confirmed by TLC (EtOAc/$CHCl_3$/Hexane=1:2:10). When the reaction was completed, the reactant was cooled down to room temperature, followed by further cooling down with the gentle addition of ice. The pH of the resulting mixture was then adjusted to 10 by dropwise addition of an aqueous solution of 4 N NaOH. When the pH was adjusted to 10, the reaction mixture was extracted with distilled water and dichloromethane, to thereby separate an organic layer. The organic layer was dried over anhydrous $MgSO_4$ and filtered. The resulting filtrate was concentrated under reduced pressure and purified by column chromatography (EtOAc/$CHCl_3$/Hexane=1:2:10, R.f: 0.6), to thereby obtain 2-chloro-5-methoxyquinoline (40.1 mg, 32%) as a white solid.

$^1$H NMR ($CDCl_3$, 300 MHz) δ 4.01 (s, 3H), 6.88 (dd, J=7.2, 1.5 Hz, 1H), 7.35 (d, J=8.7 Hz, 1H), 7.59-7.67 (m, 2H), 8.51 (d, J=8.7 Hz, 1H)

Example 2

2-Chloro-5-ethoxyquinoline

2-Chloro-5-ethoxyquinoline (68.1 mg, 45%) was obtained as a white solid according to the same method as described in Example 1 except that 5-ethoxyquinoline (128 mg, 0.74 mmol), meta-chloroperbenzoic acid (mCPBA; 208 mg, 1.21 mmol), phosphorous oxychloride ($POCl_3$; 0.10 mL, 1.06 mmol), and dichloromethane (6.0 mL) were used.

$^1$H NMR ($CDCl_3$, 300 MHz) δ 1.54 (t, J=7.2 Hz, 3H), 4.19 (q, J=6.9 Hz, 2H), 6.83 (dd, J=6.6, 2.1 Hz, 1H), 7.30-7.34 (m, 1H), 7.56-7.64 (m, 2H), 8.51 (d, J=8.7 Hz, 1H); $^{13}$C NMR ($CDCl_3$, 100 MHz) δ 14.7, 64.2, 105.6, 119.4, 120.4, 121.1, 130.8, 134.1, 148.8, 151.1, 154.6; GC/MS (EI): m/z: calcd for $C_{11}H_{10}ClNO$: 207.05, [M+H]$^+$. found: 207.

Example 3

2-Chloroquinoline-5-ylpivalate

2-Chloro-5-ethoxyquinoline (104 mg, 37%) was obtained as a white solid according to the same method as described in Example 1 except that quinoline-5-ylpivalate (245 mg, 1.07 mmol), meta-chloroperbenzoic acid (mCPBA; 368 mg, 2.13 mmol), phosphorous oxychloride ($POCl_3$; 0.15 mL, 1.60 mmol), and dichloromethane (10.0 mL) were used.

$^1$H NMR ($CDCl_3$, 300 MHz) δ 1.48 (s, 9H), 7.31 (dd, J=7.7, 0.9 Hz, 1H), 7.41 (d, J=8.8 Hz, 1H), 7.73 (t, J=8.1 Hz, 1H), 7.92 (d, J=8.6 Hz, 1H), 8.11 (d, J=8.8 Hz, 1H); $^{13}$C NMR ($CDCl_3$, 100 MHz) δ 27.3, 39.6, 119.1, 121.1, 122.6, 126.3, 130.2, 132.8, 146.5, 148.5, 151.3, 176.7

Example 4

2,5-Dichloroquinoline 2,5-Dichloroquinoline (391 mg, 47%) was obtained as a white solid according to the same method as described in Example 1 except that 5-chloroquinoline (690 mg, 4.22 mmol), meta-chloroperbenzoic acid (mCPBA; 1.10 g, 6.37 mmol), phosphorous oxychloride ($POCl_3$; 0.60 mL, 6.33 mmol), and dichloromethane (35 mL) were used.

$^1$H NMR ($CDCl_3$, 300 MHz) δ 7.49 (d, J=8.8 Hz, 1H), 7.61-7.69 (m, 2H), 7.92-7.99 (m, 1H), 8.52 (d, J=8.8 Hz, 1H); $^{13}$C NMR ($CDCl_3$, 100 MHz) δ 123.3, 125.2, 127.1, 127.8, 130.4, 131.5, 135.9, 148.5, 151.7

Example 5

5-Bromo-2-chloroquinoline

5-Bromo-2-chloroquinoline (54.4 mg, 45%) was obtained as a white solid according to the same method as described in Example 1 except that 5-bromoquinoline (103 mg, 0.496 mmol), meta-chloroperbenzoic acid (mCPBA; 133 mg, 0.768 mmol), phosphorous oxychloride ($POCl_3$; 0.07 mL, 0.744 mmol), and dichloromethane (5.0 mL) were used.

$^1$H NMR ($CDCl_3$, 300 MHz) δ 7.45 (d, J=8.8 Hz, 1H), 7.57 (dd, J=8.3, 7.8 Hz, 1H), 7.80 (dd, J=7.5, 0.9 Hz, 1H), 7.97 (d, J=8.5 Hz, 1H), 7.97 (d, J=8.5 Hz, 1H), 8.45 (d, J=8.8 Hz, 1H); $^{13}$C NMR ($CDCl_3$, 75 MHz) δ 121.8, 123.6, 126.5, 128.5, 130.8, 130.9, 138.5, 148.5, 151.7; GC/MS (EI): m/z: calcd for $C_9H_5BrClN$: 240.93, [M+H]$^+$. found: 243

Example 6

2-Methyl-4-(quinoline-2-)but-3-yn-2-ol

2-Chloroquinoline (50.4 mg, 3.04 mmol), $PdCl_2(PPh_3)_2$ (11.2 mg, 0.0160 mmol), and CuI (6.2 mg, 0.0326 mmol) were dissolved in triethylamine (0.61 mL), followed by stirring for 5 min under nitrogen atmosphere. Five minutes after, 2-methyl-3-butyn-2-ol (0.0442 ml, 0.456 mmol) was added thereto, and the resulting mixture was refluxed at 80° C. The completion of the reaction was confirmed by TLC (EtOAc/Hexane=1:1). When the reaction was completed, the reactant was cooled down to room temperature and filtered through Celite. The thus obtained filtrate was extracted with ethyl acetate, to thereby obtain an organic layer. The organic layer was dried over anhydrous $MgSO_4$ and filtered. The thus obtained filtrate was concentrated under reduced pressure and purified with column chromatography (EtOAc/Hexane=1:1, R.f: 0.5), to thereby obtain 2-methyl-4-(quinoline-2-yl)but-3-yn-2-ol (59.7 mg, 100%) as a yellow solid.

$^1$H NMR ($CDCl_3$, 300 MHz) δ 7.39 (d, J=11.2 Hz, 1H)), 7.46 (m, 1H), 7.66 (m, 2H), 8.00 (d, J=8.4 Hz, 1H), 8.10. (d, J=8.5 Hz, 1H); $^{13}$C NMR ($CDCl_3$, 100 MHz) δ 31.3, 65.3, 82.0, 95.4, 124.3, 127.1, 127.5, 129.1, 130.1, 136.2, 143.2, 147.9.

Example 7

4-(5-Chloroquinoline-2-yl)-2-methylbut-3-yn-2-ol 4-(5-Chloroquinoline-2-yl)-2-methylbut-3-yn-2-ol (191 mg, 93%) was obtained as yellow oil according to the same method as described in Example 6 except that 2,5-dichloroquinoline (165.5 mg, 0.83 mmol), CuI (19.3 mg, 0.099 mmol), $PdCl_2(PPh_3)_2$ (59.1 mg, 0.084 mmol), 2-methyl-3-butyn-2-ol (0.13 mL, 1.33 mmol), and triethylamine (1.7 mL) were used.

$^1$H NMR ($CDCl_3$, 400 MHz) δ 1.69 (s, 6H), 2.37 (brs, 1H), 7.57-7.65 (m, 3H), 8.03 (dd, J=5.2, 1.9 Hz, 1H), 8.52 (d, J=6.3

Hz, 1H); $^{13}$C NMR (CDCl$_3$, 75 MHz) δ 31.22, 65.4, 81.7, 96.0, 125.1, 125.2, 127.1, 128.3, 129.8, 131.2, 133.1, 144.0, 148.5.

Example 8

4-(5-Bromoquinoline-2-yl)-2-methylbut-3-yn-2-ol 4-(5-Bromoquinoline-2-yl)-2-methylbut-3-yn-2-ol (191 mg, 52%) was obtained as brown oil according to the same method as described in Example 6 except that 5-bromo-2-chloroquinoline (96.4 mg, 0.40 mmol), CuI (8.7 mg, 0.045 mmol), PdCl$_2$(PPh$_3$)$_2$ (14.4 mg, 0.021 mmol), 2-methyl-3-butyn-2-ol (0.05 mL, 0.52 mmol), and triethylamine (0.8 mL) were used.

$^1$H NMR (CDCl$_3$, 400 MHz) δ 1.68 (s, 1H), 2.28 (brs, 1H), 7.54-7.59 (m, 2H), 7.81 (dd, J=10.0, 1.2 Hz, 1H), 8.06 (d, J=8.7 Hz, 1H), 8.48 (d, J=8.7 Hz, 1H); $^{13}$C NMR (CDCl$_3$, 75 MHz) δ 31.2, 65.4, 81.6, 96.0, 121.7, 125.3, 126.6, 129.1, 130.3, 130.8, 135.7, 144.0, 148.6; GC/MS (EI): m/z: calcd for C$_{14}$H$_{12}$BrNO: 289.01, [MiPrOH]$^+$. found: 231

Example 9

2-((Trimethylsilyl)ethynyl)quinoline

2-Chloroquinoline (1.02 g, 6.17 mmol), CuI (12.1 mg, 0.622 mmol), and PdCl$_2$(PPh$_3$)$_2$ (22.7 mg, 0.0317 mmol) were dissolved in triethylamine (20.6 mL), followed by stirring for 5 min. To the resulting mixture, trimethylsilyl acetylene (1.34 mL, 9.44 mmol) was added dropwise at 60° C., followed by heating. The completion of the reaction was confirmed by TLC (EtOAc/Hexane=1:10). When the reaction was completed, the reactant was cooled down to room temperature and extracted with a saturated aqueous solution of NaCl and ethyl acetate, to thereby separate an organic layer. The organic layer was dried over anhydrous MgSO$_4$ and filtered. The filtrate was concentrated under reduced pressure and purified by column chromatography (EtOAc/Hexane=1:10, R.f: 0.4), to thereby obtain 2-((trimethylsilyl)ethynyl)quinoline (1.289 g, 93%) as brown oil.

$^1$H NMR (CDCl$_3$, 400 MHz) δ 0.20 (s, 1H), 7.31 (ddd, J=8.0, 1.0, 1.0 Hz, 1H), 7.33 (d, J=8.4 Hz), 7.50-7.54 (m, 2H), 7.85 (d, J=8.4 Hz, 1H), 7.97 (dd, J=8.0, 1.0 Hz, 1H); $^{13}$C NMR (MeOD, 100 MHz) δ −1.7, 95.7, 103.6, 124.0, 127.3, 127.4, 127.5, 127.6, 130.3, 137.1, 142.6, 147.3.

Example 10

2-Ethynylquinoline 2-((Trimethylsilyl)ethynyl)quinoline (1.289 g, 5.72 mmol), and K$_2$CO$_3$ (0.792 g, 5.73 mmol) were dissolved in a mixture of methanol (3 mL) and dichloromethane (1.5 mL), followed by stirring at room temperature. The completion of the reaction was confirmed by TLC (EtOAc/Hexane=1:4). When the reaction was completed, the pH of the reactant was adjusted to 10 by addition of an aqueous solution of 1 M HCl and extracted with dichloromethane, to thereby separate an organic layer. The organic layer was dried over anhydrous MgSO$_4$ and filtered. The thus obtained filtrate was concentrated under reduced pressure and purified by column chromatography (EtOAc/Hexane=1:4, R.f: 0.3), to thereby obtain 2-ethynylquinoline (0.742 g, 85%) as brown oil.

$^1$H NMR (CDCl$_3$, 400 MHz) δ 3.24 (s, 1H), 7.52 (d, J=8.5 Hz, 1H), 7.53 (ddd, J=8.1, 7.0, 1.1 Hz, 1H), 7.71 (ddd, J=8.4, 6.9, 1.4 Hz, 1H) 7.77 (dd, J=8.2, 1.0 Hz, 1H), 8.08 (dd, J=7.6, 0.76 Hz, 1H), 8.10 (d, J=6.4 Hz, 1H); $^{13}$C NMR (CDCl$_3$, 100 MHz) δ 77.2, 77.6, 83.4, 124.2, 127.4, 127.5, 129.5, 130.2, 136.3, 142.4, 148.1.

Example 11

2-(Phenylethynyl)quinoline

After 2-chloroquinoline (29.7 mg, 0.182 mmole) was dissolved in THF (1.5 mL), PdCl$_2$(PPh$_3$)$_2$ (2.6 mg, 0.0037 mmole), and CuI (1.5 mg, 0.0063 mmol) were added thereto and stirred for 5 min under nitrogen atmosphere. To the resulting mixture triethylamine (0.15 mL) and phenylacetylene (0.03 mL, 0.273 mmol) were successively added, followed by stirring at 80° C. for 24 hr after sealing. The completion of the reaction was confirmed by TLC (EtOAc/Hexane=1:10). When the reaction was completed, the reactant was filtered through Celite and extracted with a mixture of EtOAc and H$_2$O, to thereby separate an organic layer. The organic layer was dried over anhydrous MgSO$_4$, concentrated under reduced pressure, and purified by column chromatography (EtOAc/Hexane=1:10, R.f: 0.35), to thereby obtain 2-(phenylethynyl)quinoline (24.9 mg, 60%) as a brown solid.

$^1$H NMR (CDCl$_3$, 300 MHz) δ 7.36-7.40 (m, 3H), 7.54 (ddd, J=15.0, 6.9, 1.1 Hz, 1H), 7.60 (d, J=8.4 Hz, 1H), 7.65-7.68 (m, 2H), 7.73 (ddd, J=15.4, 6.9, 1.4 Hz, 1H), 7.80 (dd, J=8.1, 1.1 Hz, 1H), 8.13 (d, J=8.6 Hz, 1H), 8.13 (d, J=8.4 Hz, 1H); $^{13}$C NMR (CDCl$_3$, 75 MHz) δ 89.4, 89.9, 122.2, 124.4, 127.1, 127.5, 128.4, 129.2, 129.4, 130.1, 132.3, 136.2, 143.7, 148.3; GC/MS (EI): m/z: calcd for C$_{17}$H$_{11}$N: 229.09, [M+H]$^+$. found: 229.

Example 12

5-Chloro-2-(pyridine-2-ylethynyl)quinoline 4-(5-Chloroquinoline-2-yl)-2-methylbut-3-yn-2-ol (24.5 mg, 0.0997 mmol), PdCl$_2$(PPh$_3$)$_2$ (3.4 mg, 0.00484 mmol), CuI (1.2 mg, 0.00875 mmol), and KOH (44.6 mg, 0.795 mmol) were dissolved in diisopropylamine (0.2 mL) in a vial. The resulting mixture was stirred for 5 min under nitrogen atmosphere, followed by adding 2-bromopyridine (9.6 uL, 0.0997 mmol) thereto. After the vial was capped, it was heated to 110° C. The completion of the reaction was confirmed by TLC (EtOAc/Hexane=1:1). When the reaction was completed, the reactant was cooled down to room temperature and filtered through Celite and ethyl acetate. The thus obtained filtrate was extracted with ethyl acetate, to thereby obtain an organic layer. The organic layer was dried over anhydrous MgSO$_4$ and filtered. The filtrate was concentrated under reduced pressure and purified by column chromatography (EtOAc/Hexane=1:1, R.f: 0.3), to thereby obtain 5-chloro-2-(pyridine-2-ylethynyl)quinoline (6.2 mg, 25%) as a brown solid.

$^1$H NMR (CDCl$_3$, 400 MHz) δ 7.32 (m, 1H), 7.65 (m, 2H), 7.70 (m, 2H), 7.79 (d, J=8.7 Hz, 1H), 8.06 (dd, J$_1$=7.0 Hz, J$_2$=2.5 Hz, 1H), 8.59 (d, J=8.7 Hz, 1H), 8.68 (d, J=4.8 Hz, 1H); $^{13}$C NMR (CDCl$_3$, 100 MHz) δ 87.9, 89.2, 123.7, 125.4, 125.5, 127.4, 128.0, 128.7, 129.9, 131.4, 133.3, 136.3, 142.4, 143.7, 148.9, 150.3; GC/MS (EI): m/z: calcd for C$_{16}$H$_9$ClN$_2$: 264.05, M$^+$. found: 264.

Example 13

2-((3-(Trifluoromethyl)pyridine-2-yl)ethynyl)quinoline

To the solution in which 2-ethynylquinoline (50 mg, 0.33 mmol) was dissolved in triethylamine (0.4 mL), PdCl$_2$ (PPh₃)₂ (12 mg, 0.02 mmol), CuI (6 mg, 0.03 mmol), and 2-bromo-3-trifluoromethylpyridine (110 mg, 0.5 mmol) were added, followed by stirring at 85° C. for 3 hr. The completion of the reaction was confirmed by TLC (EtOAc/Hexane=1:1). The reactant was cooled down to room temperature and filtered through Celite. The thus obtained filtrate was extracted with EtOAc (3×10 mL), to thereby obtain an organic layer. The organic layer was washed with a saturated aqueous solution of NaCl. The organic layer was then dried over anhydrous $MgSO_4$, concentrated under reduced pressure, and purified by column chromatography (EtOAc/hexane=1:1), to thereby obtain 2-((3-(trifluoromethyl)pyridine-2-yl)ethynyl)quinoline (48 mg, 49%) as a brown solid.

$^1$H NMR (400 MHz, $CDCl_3$) δ 7.47-7.43 (t, J=4 Hz, 1H), 7.62-7.58 (td, J=7.5, 1.1 Hz, 1H), 7.71-7.69 (d, J=8.4 Hz, 1H), 7.79-7.75 (td, J=5.6, 2.9 Hz, 1H), 7.85-7.83 (d, J=8.4 Hz, 1H), 8.06-8.04 (d, J=8 Hz, 1H), 8.21-8.16 (t, J=9.6 Hz, 2H), 8.85-8.84 (d, J=4.8 Hz, 1H); $^{13}$C NMR (100 MHz, $CDCl_3$) δ 84.4, 93.7, 121.1, 122.7, 124.5, 127.6, 129.2, 129.7, 130.2, 133.8, 133.9, 136.2, 140.5, 142.2, 148.4, 152.6, 162.3; GC/MS (EI): m/z: calcd for $C_{17}H_9F_3N_2$: 298.07, M⁺. found: 298.

Example 14

5-Methoxy-2-(phenylethynyl)quinoline

5-Methoxy-2-(phenylethynyl)quinoline was prepared according to the same method as described in Example 11.

Yield 60%, White powder: $^1$H NMR ($CDCl_3$, 300 MHz) δ 4.05 (s, 3H), 6.91 (d, J=7.5 Hz, 1H), 7.42-7.44 (m, 3H), 7.62-7.77 (m, 5H), 8.60 (d, J=8.7 Hz, 1H); $^{13}$C NMR ($CDCl_3$, 100 MHz) δ 55.8, 89.4, 89.9, 104.8, 119.6, 121.5, 122.2, 123.5, 128.4, 129.1, 130.0, 131.0, 132.3, 143.9, 149.1, 155.0; GC/MS (EI): m/z: calcd for $C_{18}H_{13}NO$: 259.10, M⁺. found: 259.

Example 15

2-(Phenylethynyl)quinoline-5-ylpivalate 2-(Phenylethynyl)quinoline-5-ylpivalate was prepared according to the same method as described in Example 11.

Yield 100%, White powder; $^1$H NMR ($CDCl_3$, 400 MHz) δ 1.49 (s, 9H), 7.29 (dd, J=7.6, 0.9 Hz, 1H), 7.36-7.40 (m, 3H), 7.62 (d, J=8.6 Hz, 1H), 7.66-7.69 (m, 2H), 7.72-7.75 (m, 1H), 8.02 (d, J=8.6 Hz, 1H), 8.15 (dd, J=8.7, 0.7 Hz, 1H); $^{13}$C NMR ($CDCl_3$, 75 MHz) δ 27.4, 39.6, 89.1, 90.6, 119.1, 121.2, 122.0, 124.6, 127.1, 128.5, 129.4, 129.5, 130.0, 132.3, 144.1, 146.3, 148.9, 176.8; GC/MS (EI): m/z: calcd for $C_{21}H_{18}N_2O_2$. 330.14, [M−H]⁺. found: 329.

Example 16

2-(Phenylethynyl)quinoline-5-ol 2-(Phenylethynyl)quinoline-5-ylpivalate (15.4 mg, 0.0468 mmol) was dissolved in THF (0.78 mL), followed by cooling down to 0° C. After $LiAlH_4$ (0.06 mL, 0.117 mmol) was added thereto, the resulting mixture was warmed to room temperature and stirred for 1 hr. The completion of the reaction was confirmed by TLC (EtOAc/Hexane=1:1). When the reaction was completed, a saturated aqueous solution was added thereto, and the resulting mixture was extracted with diethylether, to thereby obtain an organic layer. The organic layer was dried over anhydrous $MgSO_4$ and filtrated. The filtrate was concentrated under reduced pressure and purified by column chromatography (EtOAc/Hexane=1:1, R.f: 0.7), to thereby obtain 2-(phenylethynyl)quinoline-5-ol (5.6 mg, 49%) as a yellow solid.

$^1$H NMR (MeOD, 300 MHz) δ 6.92 (d, J=0.84 Hz, 1H), 7.42-7.49 (m, 4H), 7.55-7.68 (m, 4H), 8.66 (d, J=4.3 Hz, 1H); $^{13}$C NMR (MeOD, 75 MHz) δ 88.2, 89.9, 108.9, 118.0, 119.1, 121.8, 122.4, 128.4, 129.3, 130.8, 131.7, 132.2, 143.5, 153.5; GC/MS (EI): m/z: calcd for $C_{17}H_{12}NO$: 246.08, [M⁺+H]. found: 246.2

Example 17

5-Chloro-2-(phenylethynyl)quinoline

5-Chloro-2-(phenylethynyl)quinoline was prepared according to the same method as described in Example 11.

Yield 94%, Brown solid; $^1$H NMR ($CDCl_3$, 300 MHz) δ 7.36-7.40 (m, 3H), 7.59-7.70 (m, 5H), 8.05 (dd, J=7.4, 1.6 Hz, 1H), 8.54 (d, J=8.6 Hz, 1H); $^{13}$C NMR ($CDCl_3$, 100 MHz) δ 88.9, 90.9, 121.9, 125.2, 127.1, 128.5, 128.5, 129.4, 129.8, 131.3, 132.3, 133.0, 144.4, 148.9; GC/MS (EI): m/z: calcd for $C_{17}H_{10}ClN$: 263.05, M⁺. found: 263.

Example 18

5-Bromo-2-(phenylethynyl)quinoline

5-Bromo-2-(phenylethynyl)quinoline was prepared according to the same method as described in Example 11.

Yield 22%; Yellow solid; $^1$H NMR ($CDCl_3$, 400 MHz) δ 7.37-7.41 (m, 3H), 7.57 (dd, J=8.4, 7.6 Hz, 1H), 7.66 (m, 3H), 7.81 (dd, J=7.5, 1.0 Hz, 1H), 8.09 (d, J=8.5 Hz, 1H), 8.50 (dd, J=8.7, 0.6 Hz, 1H); $^{13}$C NMR ($CDCl_3$, 75 MHz) δ 88.8, 91.1, 121.8, 121.9, 125.5, 126.6, 128.5, 129.2, 129.4, 130.3, 130.8, 132.3, 135.7, 144.5, 148.9; GC/MS (EI): m/z: calcd for $C_{17}H_{10}BrN$: 307.00, M⁺. found: 307.

Example 19

2-(Pyridine-3-ylethynyl)quinoline 2-(Pyridine-3-ylethynyl)quinoline was prepared according to the same method as described in Example 11.

Yield 33%, Brown solid; $^1$H NMR ($CDCl_3$, 300 MHz) δ 7.37-7.41 (m, 3H), 7.57 (dd, J=8.4, 7.6 Hz, 1H), 7.66 (m, 3H), 7.81 (dd, J=7.5, 1.0 Hz, 1H), 8.09 (d, J=8.5 Hz, 1H), 8.88 (d, J=1.9 Hz, 1H); $^{13}$C NMR ($CDCl_3$, 75 MHz) δ 86.1, 92.3, 119.4, 123.1, 124.2, 127.3, 127.4, 127.6, 129.4, 130.3, 136.4, 139.1, 142.9, 148.2, 149.4, 152.8; GC/MS (EI): m/z: calcd for $C_{16}H_{10}N_2$: 230.08, M⁺. found: 230.

Example 20

5-Methoxy-2-(pyridine-3-ylethynyl)quinoline

5-Methoxy-2-(pyridine-3-ylethynyl)quinoline was prepared according to the same method as described in Example 11.

Yield 57%, White powder; $^1$H NMR ($CDCl_3$, 300 MHz) δ 4.05 (s, 3H), 6.92 (d, J=7.5 Hz, 1H), 7.36 (dd, J=8.0, 4.9 Hz, 1H), 7.62-7.77 (m, 3H), 7.97 (td, J=4.8, 2.6 Hz, 1H), 8.62 (d, J=10.2 Hz, 1H), 8.63-8.65 (m, 1H), 8.92 (d, J=1.2 Hz, 1H); $^{13}$C NMR ($CDCl_3$, 100 MHz) δ 55.8, 86.1, 92.4, 105.1, 119.5, 119.8, 121.5, 123.1, 130.2, 131.3, 139.1, 143.2, 149.0, 149.4, 152.8, 155.0; GC/MS (EI): m/z: calcd for $C_{17}H_{12}N_2O$: 260.09, M⁺. found: 260

Example 21

5-Ethoxy-2-(pyridine-3-ylethynyl)quinoline

5-Ethoxy-2-(pyridine-3-ylethynyl)quinoline was prepared according to the same method as described in Example 11.

Yield 56%, Yellow solid; $^1$H NMR (CDCl$_3$, 300 MHz) δ 1.52 (t, J=7.0 Hz, 3H), 4.19 (q, J=7.0 Hz, 2H), 6.83 (d, J=7.6 Hz, 1H), 7.29 (dd, J=7.8, 5.0 Hz, 1H), 7.55-7.61 (m, 2H), 7.67 (d, J=8.5 Hz, 1H), 7.91 (d, J=7.9 Hz, 1H), 8.58-8.60 (m, 1H), 8.87 (s, 1H); $^{13}$C NMR (CDCl$_3$, 100 MHz) δ 14.7, 64.1, 86.0, 92.4, 105.8, 119.5, 119.9, 121.2, 123.1, 123.2, 130.3, 131.4, 139.0, 143.1, 149.1, 149.3, 152.8, 154.3; GC/MS (EI): m/z: calcd for C$_{18}$H$_{14}$N$_2$O: 274.11, M$^+$. found: 274

Example 22

2-(Pyridine-3-ylethynyl)quinoline-5-ylpivalate 2-(Pyridine-3-ylethynyl)quinoline-5-ylpivalate was prepared according to the same method as described in Example 11.

Yield 69%, White powder; $^1$H NMR (CDCl$_3$, 300 MHz) δ 1.50 (s, 9H), 7.31-7.36 (m, 2H), 7.63 (d, J=8.6 Hz, 1H), 7.74 (t, J=8.5 Hz, 1H), 7.95 (td, J=4.9, 2.6 Hz, 1H), 8.03 (d, J=8.6 Hz, 1H), 8.19 (d, J=4.3 Hz, 1H), 7.95 (dd, J=2.4, 1.4 Hz, 1H), 8.90 (d, J=1.3 Hz, 1H); $^{13}$C NMR (CDCl$_3$, 75 MHz) δ 27.4, 39.6, 86.8, 92.1, 119.4, 121.5, 123.2, 124.4, 127.1, 129.7, 130.2, 139.2, 139.4, 143.4, 146.3, 148.9, 149.5, 152.8, 176.8; GC/MS (EI): m/z: calcd for C$_{21}$H$_{18}$N$_2$O$_2$: 330.14, M$^+$. found: 330

Example 23

2-(Pyridine-3-ylethynyl)quinoline-5-ol 2-(Pyridine-3-ylethynyl)quinoline-5-ol (8.5 mg, 29%) was prepared as a yellow solid according to the same method as described in Example 16 except that 2-(pyridine-3-ylethynyl)quinoline-5-ylpivalate (40 mg, 0.121 mmol), LiAlH$_4$ (0.3 mL, 1.0 M in THF), and THF (2.0 mL) were used.

$^1$H NMR (CDCl$_3$, 300 MHz) δ 6.90 (d, J=7.1 Hz, 1H), 7.29-7.33 (m, 2H), 7.54 (t, J=8.2 Hz, 1H), 7.60 (d, J=8.7 Hz, 1H), 7.70 (d, J=8.6 Hz, 1H), 7.87-7.90 (m, 1H), 8.58-8.62 (m, 2H), 8.85 (brs, 1H); $^{13}$C NMR (CDCl$_3$, 100 MHz) δ 108.5, 117.6, 118.6, 119.3, 122.7, 123.2, 130.3, 132.1, 132.4, 133.5, 137.4, 149.1, 153.5, 154.8, 156.3, 162.3; GC/MS (EI): m/z: calcd for C$_{16}$H$_{13}$N$_2$O: 247.08, [M$^+$+H]. found: 247.1

Example 24

5-Chloro-2-(pyridine-3-ylethynyl)quinoline

5-Chloro-2-(pyridine-3-ylethynyl)quinoline was prepared according to the same method as described in Example 11.

Yield 48%, White powder; $^1$H NMR (CDCl$_3$, 400 MHz) δ 7.36-7.40 (m, 3H)), 7.59-7.70 (m, 5H), 8.05 (dd, J=7.4, 1.6 Hz, 1H), 8.54 (d, J=8.6 Hz, 1H); $^{13}$C NMR (CDCl$_3$, 100 MHz) δ 87.1, 91.9, 119.2, 123.2, 125.0, 125.4, 127.4, 128.6, 130.0, 131.3, 133.3, 139.2, 143.7, 148.8, 149.5, 152.7; GC/MS (EI): m/z calcd for C$_{16}$H$_9$ClN$_2$: 264.05, M$^+$. found: 264.

Example 25

5-Bromo-2-(pyridine-3-ylethynyl)quinoline

5-Bromo-2-(pyridine-3-ylethynyl)quinoline was prepared according to the same method as described in Example 11.

Yield 22%, Yellow solid; $^1$H NMR (CDCl$_3$, 400 MHz) δ 7.32 (dd, J=7.8, 4.9 Hz, 1H)), 7.58 (dd, J=8.3, 7.7 Hz, 1H), 7.69 (d, J=8.7 Hz, 1H), 7.82 (dd, J=7.5, 0.8 Hz, 1H), 7.93. (td, J=4.9, 2.6 Hz, 1H), 8.08 (d, J=8.5 Hz, 1H), 8.53 (d, J=8.5 Hz, 1H), 8.61. (dd, J=4.7, 1.2 Hz, 1H), 8.89 (brs, 1H); $^{13}$C NMR (CDCl$_3$, 100 MHz) δ 87.1, 91.8, 119.2, 121.8, 123.2, 125.4, 126.7, 129.3, 130.5, 131.1, 135.9, 139.2, 143.7, 148.9, 149.6, 152.8; GC/MS (EI): m/z: calcd for C$_{16}$H$_{10}$BrN$_2$: 307.99, [M$^+$+H]. found: 309; purity (HPLC) 97.40%.

Example 26

2-(Pyridine-2-ylethynyl)quinoline 2-(Pyridine-2-ylethynyl)quinoline was prepared according to the same method as described in Example 11.

Yield 37%, Green solid; $^1$H NMR (CDCl$_3$, 300 MHz) δ 7.31-7.34 (m, 1H), 7.59 (dd, J=7.8, 7.2 Hz, 1H), 7.70-7.79 (m, 4H), 7.84 (d, J=8.4 Hz, 1H), 8.17 (t, J=8.7 Hz, 2H), 8.69 (d, J=4.8 Hz, 1H); $^{13}$C NMR (CDCl$_3$, 75 MHz) δ 88.3, 88.4, 123.5, 124.6, 127.4, 127.5, 127.6, 128.0, 129.4, 130.2, 136.3, 136.3, 142.5, 142.8, 148.2, 150.3; GC/MS (EI): m/z: calcd for C$_{16}$H$_{10}$N$_2$: 230.08, M$^+$. found: 230.

Example 27

2-(Pyridine-2-ylethynyl)quinoline-5-ylpivalate 2-(Pyridine-2-ylethynyl)quinoline-5-ylpivalate was prepared according to the same method as described in Example 11.

Yield 31%, White powder; $^1$H NMR (CDCl$_3$, 300 MHz) δ 1.49 (s, 9H), 7.25-7.30 (m, 2H), 7.67-7.73 (m, 4H), 8.00 (d, J=8.61 Hz, 1H), 8.15 (d, J=8.6 Hz, 1H), 8.63-8.65 (m, 1H); $^{13}$C NMR (CDCl$_3$, 75 MHz) δ 27.4, 39.6, 88.2, 88.9, 119.4, 121.5, 123.7, 124.8, 127.2, 128.1, 129.6, 130.2, 136.3, 142.5, 143.3, 146.3, 148.9, 150.3, 176.8; GC/MS (EI): m/z: calcd for C$_{21}$H$_{18}$N$_2$O$_2$: 330.14, M$^+$. found: 329

Example 28

2-(Pyridine-2-ylethynyl)quinoline-5-ol 2-(Pyridine-2-ylethynyl)quinoline-5-ol (3.7 mg, 9%) was prepared as yellow solid according to the same method as described in Example 16 except that 2-(pyridine-2-ylethynyl)quinoline-5-ylpivalate (56.8 mg, 0.17 mmol), LiAlH$_4$ (0.43 mL, 1.0 M in THF), and THF (2.8 mL) were used.

$^1$H NMR (DMSO, 300 MHz) δ 6.90 (d, J=7.5 Hz, 1H), 7.34 (dd, J=7.4, 4.7 Hz, 1H), 7.45 (d, J=8.4 Hz, 1H), 7.52-7.57 (m, 1H), 7.72 (d, J=7.3 Hz, 1H), 7.81-7.87 (m, 3H), 8.50 (d, J=8.7 Hz, 1H), 8.64-8.65 (m, 1H), 8.90 (d, J=1.3 Hz, 1H); $^{13}$C NMR (MeOD, 75 MHz) δ 108.4, 117.6, 118.6, 119.3, 122.7, 123.2, 130.3, 132.1, 132.4, 133.5, 137.3, 148.7, 149.1, 153.5, 154.7, 155.3; GC/MS (EI): m/z: calcd for C$_{16}$H$_{11}$N$_2$O: 246.08, [M$^+$+H]. found: 246.2

Example 29

5-Bromo-2-(pyridine-2-ylethynyl)quinoline

5-Bromo-2-(pyridine-2-ylethynyl)quinoline was prepared according to the same method as described in Example 12.

Yield 35%, Yellow solid; $^1$H NMR (CDCl$_3$, 300 MHz) δ 7.31 (m, 1H), 7.59 (dd, J=8.4, 7.7 Hz, 1H), 7.70 (m, 2H), 7.76 (m, 1H), 7.83. (dd, J=7.5, 1.0 Hz, 1H), 8.10 (d, J=8.5 Hz, 1H), 8.54 (dd, J=8.7, 0.6 Hz, 1H), 8.67 (td, J=3.0, 1.6 Hz, 1H); $^{13}$C NMR (CDCl$_3$, 100 MHz) δ 87.8, 89.2, 121.8, 123.7, 125.7, 126.8, 128.0, 129.4, 130.4, 131.1, 135.9, 136.3, 142.4, 143.7, 148.9, 150.3; GC/MS (EI): m/z: calcd for C$_{16}$H$_9$BrN$_2$: 307.99, M$^+$. found: 308; purity (HPLC) 98.70%.

Example 30

2-((3-Fluoropyridine-2-yl)ethynyl)quinoline 2-((3-Fluoropyridine-2-yl)ethynyl)quinoline was prepared according to the same method as described in Example 12.

Yield 20%, Yellow solid; $^1$H NMR (CDCl$_3$, 400 MHz) δ 7.37-7.33 (m, 1H), 7.52-7.48 (td, J=8.5, 1.3 Hz, 1H), 7.60-7.56 (td, J=7.5, 1.3 Hz, 1H), 7.71-7.69 (d, J=8.4 Hz, 1H), 7.77-7.73 (td, J=7.7, 1.7 Hz, 1H), 7.84-7.82 (d, J=8 Hz, 1H), 8.19-8.14 (m, 2H), 8.50-8.48 (dt, J=4.7, 1.3 Hz, 1H); $^{13}$C NMR (CDCl$_3$, 100 MHz) δ 82.3, 94.2, 123.2, 123.4, 124.5, 124.9, 127.6, 129.6, 130.2, 131.7, 136.3, 142.5, 146.0, 148.3, 159.3, 161.9; GC/MS (EI): m/z: calcd for C$_{16}$H$_9$FN: 248.07, M$^+$. found: 248.

Example 31

2-((3-Methylpyridine-2-yl)ethynyl)quinoline 2-((3-Methylpyridine-2-yl)ethynyl)quinoline was prepared according to the same method as described in Example 12.

Yield 20%, Yellow solid; $^1$H NMR (CDCl$_3$, 300 MHz) δ 7.31 (m, 1H)), 7.59 (dd, J$_1$=8.4 Hz, J$_2$=7.7 Hz, 1H), 7.70 (m, 2H), 7.76 (m, 1H), 7.83. (dd, J=7.5, 1.0 Hz, 1H), 8.10 (d, J=8.5 Hz, 1H), 8.54 (dd, J=8.7, 0.6 Hz, 1H), 8.67 (td, J=3.0, 1.6 Hz, 1H); $^{13}$C NMR (CDCl$_3$, 100 MHz) δ 87.8, 89.2, 121.8, 123.7, 125.7, 126.8, 128.0, 129.4, 130.4, 131.1, 135.9, 136.3, 142.4, 143.7, 148.9, 150.3; GC/MS (EI): m/z: calcd for C$_{17}$H$_{13}$N$_2$: 245.10, [M$^+$+H]. found: 245.2.

Example 32

2-((4-(Trifluoromethyl)pyridine-2-yl)ethynyl)quinoline 2-((3-Methylpyridine-2-yl)ethynyl)quinoline was prepared according to the same method as described in Example 13.

Yield 69%, Brown solid; $^1$H NMR (400 MHz, CDCl$_3$) δ 7.52-7.51 (dd, J=4.4, 1.6 Hz, 1H), 7.61-7.57 (td, J=7.4, 1.6 Hz, 1H), 7.71-7.69 (d, J=8.4 Hz, 1H), 7.78-7.74 (td, J=7, 2.0 Hz, 1H), 7.84-7.82 (d, J=8 Hz, 1H), 7.92 (s, 1H), 8.19-8.13 (q, J=8.5 Hz, 2H), 8.85-8.84 (d, J=5.2 Hz, 1H); $^{13}$C NMR (100 MHz, CDCl$_3$) δ 86.8, 90.1, 118.9, 121.0, 123.6, 124.4, 127.5, 127.7, 129.5, 130.2, 136.4, 138.7, 139.0, 142.2, 143.9, 148.3, 151.2; GC/MS (EI): m/z: calcd for C$_{17}$H$_9$F$_3$N$_2$: 298.07, M$^+$. found: 298.

Example 33

2-(Quinoline-2-ylethynyl)isonicotinonitrile 2-(Quinoline-2-ylethynyl)isonicotinonitrile was prepared according to the same method as described in Example 13.

Yield 80%, Orange solid; $^1$H NMR (CDCl$_3$, 400 MHz) δ 7.54-7.52 (dd, J=4.8, 1.6 Hz, 1H), 7.63-7.59 (td, J=7.6, 1.2 Hz, 1H), 7.71-7.69 (d, J=8.4 Hz, 1H), 7.80-7.76 (td, J=7.8, 2.0 Hz, 1H), 7.88-7.84 (t, J=9 Hz, 2H), 8.16-8.14 (d, J=8.4 Hz, 1H), 8.22-8.20 (d, J=8 Hz, 1H), 8.86-8.84 (dd, J=5.2, 1.1 Hz, 1H); $^{13}$C NMR (CDCl$_3$, 100 MHz) δ 86.1, 90.9, 115.7, 121.1, 124.4, 124.6, 127.5, 127.6, 127.9, 129.0, 129.6, 130.4, 136.5, 141.9, 144.1, 148.3, 151.2; GC/MS (EI): m/z: calcd for C$_{17}$H$_9$N$_3$: 255.08, M$^+$. found: 255.

Example 34

2-((4-Methylpyridine-2-yl)ethynyl)quinoline 2-((4-Methylpyridine-2-yl)ethynyl)quinoline was prepared according to the same method as described in Example 12.

Yield 8%, Yellow solid; $^1$H NMR (CDCl$_3$, 400 MHz) δ 7.11 (m, 1H)), 7.53 (m, 1H), 7.64 (ddd, J=70.9, 6.9, 1.4 Hz, 1H), 7.68 (d, J=8.4 Hz, 1H), 7.81. (d, J=8.1 Hz, 1H), 8.12 (d, J=8.6 Hz, 1H), δ 8.15 (d, J=8.6 Hz, 1H), 8.15 (d, J=5.0 Hz, 1H); $^{13}$C NMR (CDCl$_3$, 100 MHz) δ 20.9, 88.1, 88.6, 124.6, 127.4, 127.6, 128.9, 129.5, 130.1, 136.2, 142.4, 143.0, 147.5, 148.3, 150.0; GC/MS (EI): m/z: calcd for C$_{17}$H$_{12}$N$_2$: 244.10, M$^+$. found: 244

Example 35

2-((5-(Trifluoromethyl)pyridine-2-yl)ethynyl)quinoline 2-((5-(Trifluoromethyl)pyridine-2-yl)ethynyl)quinoline was prepared according to the same method as described in Example 13.

Yield 28%, Brown solid; $^1$H NMR (400 MHz, CDCl$_3$) δ 7.64-7.59 (td, J$_1$=7.6, J$_2$=1.6 Hz, 1H), 7.75-7.72 (d, J=8.4 Hz, 1H), 7.82-7.77 (td, J=8.2, 2.7 Hz, 2H), 7.87-7.84 (t, J=7 Hz, 1H), 8.01-7.98 (dd, J=8.2, 1.8 Hz, 1H), 8.18-8.16 (d, J=8.8 Hz, 1H), 8.23-8.21 (d, J=8.4 Hz, 1H), 8.94 (s, 1H); $^{13}$C NMR (100 MHz, CDCl$_3$) δ 86.9, 90.7, 124.5, 125.8, 127.4, 127.5, 127.6, 127.8, 129.5, 130.4, 133.5, 133.6, 136.5, 142.1, 147.0, 147.1, 148.3; GC/MS (EI): m/z: calcd for C$_{17}$H$_9$F$_3$N$_2$: 298.07, M$^+$. found: 298.

Example 36

2-((5-Fluoropyridine-2-yl)ethynyl)quinoline 2-((5-Fluoropyridine-2-yl)ethynyl)quinoline was prepared according to the same method as described in Example 13.

Yield 46%; Gold solid; $^1$H NMR (300 MHz, CDCl$_3$) δ 7.47-7.40 (td, J=8.3, 2.9 Hz, 1H), 7.59-7.54 (td, J=7.5, 1.1 Hz, 1H), 7.66 (s, 1H), 7.72-7.68 (dt, J=8.9, 2.1 Hz, 1H), 7.77-7.72 (dd, J=6.9, 1.4 Hz, 1H), 7.82-7.80 (d, J=8.1 Hz, 1H), 8.13-8.11 (d, J=8.8 Hz, 1H), 8.18-8.15 (d, J=8.6 Hz, 1H), 8.52-8.51 (d, J=2.9 Hz, 1H); $^{13}$C NMR (100 MHz, CDCl$_3$) δ 87.3, 88.2, 123.2, 123.4, 124.5, 127.6, 129.0, 129.5, 130.2, 136.4, 138.7, 138.8, 139.2, 142.7, 148.3, 157.2; GC/MS (EI): m/z: calcd for C$_{16}$H$_9$FN: 248.07, M$^+$. found: 248.

Example 37

2-((5-Methylpyridine-2-yl)ethynyl)quinoline 2-((5-Methylpyridine-2-yl)ethynyl)quinoline was prepared according to the same method as described in Example 12.

Yield 32%, Brown solid; $^1$H NMR (CDCl$_3$, 400 MHz) δ 7.48 (dd, J=4.8, 3.2 Hz, 1H), 7.50 (ddd, J=5.6, 2.2, 1.0 Hz, 1H), 7.56 (d, J=7.9 Hz, 1H), 7.65 (d, J=8.4 Hz, 1H), 7.70. (ddd, J=6.9, 3.6, 1.4 Hz, 1H), 8.10 (m, 2H), 8.46 (dd, J=1.3, 0.7 Hz, 1H); $^{13}$C NMR (CDCl$_3$, 100 MHz) δ 18.6, 87.9, 88.6, 124.5, 127.3, 127.3, 127.4, 127.6, 129.4, 130.1, 133.6, 136.2, 136.7, 139.7, 143.0, 148.2, 150.8; GC/MS (EI): m/z: calcd for C$_{17}$H$_{12}$N$_2$: 244.10, M$^+$. found: 244; purity (HPLC) 95.42%.

Example 38

2-((6-(Trifluoromethyl)pyridine-2-yl)ethynyl)quinoline 2-((6-(Trifluoromethyl)pyridine-2-yl)ethynyl)quinoline was prepared according to the same method as described in Example 13.

Yield 50%, Yellow solid; $^1$H NMR (400 MHz, CDCl$_3$) δ 7.58-7.53 (td, J=7.6, 1.5 Hz, 1H), 7.69-7.64 (m, 2H), 7.75-7.71 (td, J=7.7, 1.3 Hz, 1H), 7.83-7.79 (t, J=9 Hz, 2H), 7.91-7.87 (t, J=7.8 Hz, 1H), 8.12-810 (d, J=8.4 Hz, 1H), 8.17-8.14 (d, J=8.4 Hz, 1H); $^{13}$C NMR (100 MHz, CDCl$_3$) δ 86.8, 90.0, 119.7, 120.0, 122.4, 124.5, 127.5, 127.6, 129.5, 130.3, 136.4, 137.8, 142.3, 143.1, 148.2, 148.6, 149.0; GC/MS (EI): m/z: calcd for C$_{17}$H$_9$F$_3$N$_2$: 298.07, M$^+$. found: 298.

Example 39

6-(Quinoline-2-ylethynyl)picolinonitrile 6-(Quinoline-2-ylethynyl)picolinonitrile was prepared according to the same method as described in Example 13.

Yield 77%, Yellow solid; $^1$H NMR (400 MHz, CDCl$_3$) δ 7.58-7.54 (t, J=7.6 Hz, 1H), 7.68-7.63 (m, J=7.6 Hz, 2H), 7.75-7.7 (t, J=7.6 Hz, 1H), 7.81-7.79 (d, J=8.4 Hz, 2H), 7.85-7.83 (d, J=7.2 Hz, 1H), 8.11-8.09 (d, J=8.4 Hz, 1H), 8.17-8.15 (d, J=8.4 Hz, 1H); $^{13}$C NMR (100 MHz, CDCl$_3$) δ 86.8, 90.1, 118.3, 121.0, 123.6, 124.4, 126.4, 127.5, 127.7, 129.5, 130.3, 136.4, 138.7, 139.0, 142.1, 143.9, 148.3, 151.2; GC/MS (EI): m/z: calcd for C$_{17}$H$_9$N$_3$: 255.08, M$^+$. found: 255.

Example 40

2-((6-Fluoropyridine-2-yl)ethynyl)quinoline 2-((6-Fluoropyridine-2-yl)ethynyl)quinoline was prepared according to the same method as described in Example 12.

Yield 47%, Brown solid; $^1$H NMR (400 MHz, CDCl$_3$) δ 6.94-6.92 (dd, J=8.4, 2.8 Hz, 1H), 7.56-7.52 (m, 2H), 7.65-7.63 (d, J=8.4 Hz, 1H), 7.73-7.69 (td, J=7.7, 1.5 Hz, 1H), 7.81-7.75 (q, J=8 Hz, 2H), 8.10-8.08 (d, J=8.8 Hz, 1H), 8.14-8.12 (d, J=8.4 Hz, 1H); $^{13}$C NMR (100 MHz, CDCl$_3$) δ 86.8, 89.4, 110.1, 110.6, 124.5, 125.5, 127.6, 129.5, 130.3, 136.4, 140.4, 141.4, 142.4, 148.3, 161.4, 164.6; GC/MS (EI): m/z calcd for C$_{16}$H$_9$FN$_2$: 248.07, M$^+$. found: 248.

Example 41

2-((6-Methoxypyridine-2-yl)ethynyl)quinoline 2-((6-Methoxypyridine-2-yl)ethynyl)quinoline was prepared according to the same method as described in Example 13.

Yield 62%, Orange solid; $^1$H NMR (400 MHz, CDCl$_3$) δ 3.99 (s, 3H), 6.77-6.75 (dd, J=8.4, 0.8 Hz, 1H), 7.29-7.28 (dd, J=7.2, 0.8 Hz, 1H), 7.59-7.54 (m, 2H), 7.68-7.66 (d, J=8.4 Hz, 1H), 7.76-7.72 (td, J=7.7, 1.3 Hz, 1H), 7.82-7.79 (dd, J=P 8.0, 1.2 Hz, 1H), 8.16-6.12 (t, J=7.7 Hz, 2H); $^{13}$C NMR (100 MHz, CDCl$_3$) δ 53.4, 53.7, 87.9, 88.7, 112.0, 121.5, 124.5, 127.3, 127.5, 129.4, 130.1, 136.2, 138.5, 139.4, 143.0, 148.3, 163.9; GC/MS (EI): m/z: calcd for C$_{17}$H$_{12}$N$_2$O: 260.09, M$^+$. found: 260.

Example 42

2-(Pyrimidine-2-ylethynyl)quinoline 2-(Pyrimidine-2-ylethynyl)quinoline was prepared according to the same method as described in Example 13.

Yield 29%: Brown solid; $^1$H NMR (CDCl$_3$, 400 MHz) δ 7.29 (t, J=7.9 Hz, 1H), 7.57 (ddd, J=8.1, 7.0, 1.2 Hz, 1H), 7.70 (d, J=8.4 Hz, 1H), 7.75 (ddd, J=8.4, 6.9, 1.4 Hz, 1H), 7.82 (d, J=8.2 Hz, 1H), 8.13 (d, J=8.5 Hz, 1H), 8.17 (d, J=8.5 Hz, 1H), 8.78 (d, J=5.0 Hz, 1H); $^{13}$C NMR (CDCl$_3$ 100 MHz) δ 86.5, 86.9, 120.3, 124.5, 127.6, 127.7, 129.7, 130.2, 136.2, 142.0, 148.3, 152.9, 157.4; GC/MS (EI): m/z: calcd for C$_{15}$H$_9$N$_3$: 231.08, M$^+$. found: 231.

Example 43

2-((4-(Trifluoromethyl)pyrimidine-2-yl)ethynyl)quinoline 2-((4-(Trifluoromethyl)pyrimidine-2-yl)ethynyl)quinoline was prepared according to the same method as described in Example 13.

Yield 12%, Dark brown solid; $^1$H NMR (CDCl$_3$, 400 MHz) δ 7.29 (t, J=7.9 Hz, 1H), 7.57 (ddd, J=8.1, 7.0, 1.2 Hz, 1H), 7.70 (d, J=8.4 Hz, 1H), 7.75 (ddd, J=8.4, 6.9, 1.4 Hz, 1H), 7.82 (d, J=8.2 Hz, 1H), 8.13 (d, J=8.5 Hz, 1H), 8.17 (d, J=8.5 Hz, 1H), 8.78 (d, J=5.0 Hz, 1H); $^{13}$C NMR (CDCl$_3$, 100 MHz) δ 85.8, 88.4, 115.7, 115.8, 121.4, 124.5, 127.6, 127.7, 128.0, 129.8, 130.4, 136.4, 141.5, 148.4, 153.2, 156.1, 157.4, 159.7; GC/MS (EI): m/z: calcd for C$_{16}$H$_8$F$_3$N$_3$: 299.07, M$^+$. found: 299.

Example 44

2-((5-Fluoropyrimidine-2-yl)ethynyl)quinoline 2-((5-Fluoropyrimidine-2-yl)ethynyl)quinoline was prepared according to the same method as described in Example 13.

Yield 11%, Dark brown solid; $^1$H NMR (CDCl$_3$, 300 MHz) δ 7.57-7.63 (m, 1H), 7.76 (ddd, J=12.0, 8.2, 1.8 Hz, 1H), 7.83 (d, J=10.8 Hz, 1H), 8.14 (d, J=11.3 Hz, 1H), 8.20 (d, J=11.3 Hz, 1H), 9.04 (d, J=6.7 Hz, 1H); $^{13}$C NMR (CDCl$_3$, 100 MHz) δ 86.0, 86.3, 124.4, 127.6, 127.8, 129.6, 130.3, 136.4, 141.9, 145.4, 145.6, 148.3, 148.6, 148.7, 155.3, 158.0; GC/MS (EI): m/z: calcd for $C_{15}H_8FN_3$: 249.07, M$^+$. found: 249.

Example 45

2-(Pyrimidine-5-ylethynyl)quinoline 2-(Pyrimidine-5-ylethynyl)quinoline was prepared according to the same method as described in Example 13.

Yield 32%, White powder; $^1H$ NMR (CDCl$_3$, 400 MHz) δ 7.58 (ddd, J=8.0, 7.0, 1.0 Hz, 1H), 7.62 (d, J=8.4 Hz, 1H), 7.76 (ddd, J=8.4, 7.0, 1.0 Hz, 1H), 7.82 (d, J=8.2 Hz, 1H), 8.13 (d, J=8.4 Hz, 1H), 8.19 (d, J=8.4 Hz, 1H), 8.67 (s, 2H), 9.19 (s, 1H); $^{13}C$ NMR (CDCl$_3$, 100 MHz) δ 82.2, 95.7, 119.0, 124.1, 127.5, 127.6, 127.8, 129.5, 130.4, 136.5, 142.2, 148.3, 157.4, 159.2; GC/MS (EI): m/z: calcd for $C_{15}H_9N_3$: 231.08, M$^+$. found: 231.

Meanwhile, the novel compound represented by Formula 1 according to the present invention can be prepared into different types of formulations depending on the intended use thereof. Several methods for preparing a formulation comprising the compound represented by Formula 1 according to the present invention as an active ingredient are exemplified below, but they should not be construed as a limitation in any way.

Formulation Example

Formulation Example 1

Tablet (Direct Pressurization)

After 5.0 mg of an active ingredient was sieved, it was mixed with 14.1 mg of lactose, 0.8 mg of crospovidone USNF and 0.1 mg of magnesium stearate and pressurized, to thereby prepare a tablet.

Formulation Example 2

Tablet (Wet Assembly)

An active ingredient 5.0 mg was sieved, followed by mixing with 16.0 mg of lactose and 4.0 mg of starch. After 0.3 mg of polysorbate 80 was dissolved in pure water, a proper amount thereof was added to the active ingredient mixture prepared above, followed by granulation. After drying, the thus obtained granules were sieved and mixed with 2.7 mg of colidal silicon dioxide and 2.0 mg of magnesium stearate. The resulting granules were pressurized, to thereby obtain a tablet.

Formulation Example 3

Powder and Capsule

An active ingredient 5.0 mg was sieved, followed by mixing with 14.8 mg of lactose, 10.0 mg of polyvinyl pyrrolidone, and 0.2 mg of magnesium stearate. The resulting mixture was filled in a hard No. 5 gelatin capsule by using an appropriate device.

Formulation Example 4

Injection

An injection was prepared by mixing 100 mg of an active ingredient, 180 mg of mannitol, 26 mg of Na$_2$HPO$_4$.12H$_2$O and 2974 mg of distilled water.

Meanwhile, the compound represented by Formula 1 according to the present invention was subjected to an assay for testing its activity as an mGluR5 antagonist, as follows.

Experimental Example

Inhibitory activity (%) of the compound represented by Formula 1 on calcium mobilization developed at a high concentration of glutamate in mGluR5/HEK293 cells was measured by using a high throughput FDSS6000.

Experimental Example 1

Assay for m-GluR5 Activity Using FDSS6000

After HEK cells stably expressing m-GluR5 (Human embryonic kidney cell line; m-GluR5: Yonsei University) were prepared at a density of 4×10$^4$/Ml per well, aliquots of 100 µl from the cell suspension were distributed evenly into a 96-well plate and incubated for 18 hr at 37° C., 5% CO$_2$. The well plate was washed with a HBSS buffer to remove the culture medium, and reacted with a HBSS buffer containing a Ca$^{2+}$ fluorescent dye (FLIPR Calcium 5 assay kit: Molecular Devices) for 30 min at 37° C., 5% CO$_2$, thereby labeling with the fluorescent dye. Separately from the 96-well plate including the cells, another 96-well plate including L-glutamate (final concentration: 10 uM) capable of activating m-GluR5 and a blacking agent was prepared. Since most of cell-based HTS devices are equipped with a liquid application system for injection of a drug, but have no liquid sucking system, the blocking agent to be tested and L-glutamate were respectively provided at a 6-fold higher concentration in a HBSS buffer at the amount of 25 µl, diluted by six-times at the final cell plate volume of 150 µl, and then used in this assay. Briefly, the FDSS6000 assay was carried out by recording a reference level of 20 sec, pre-treating with a blocking agent for 75 sec, and then measuring the change in intracellular calcium level depending on the administration of L-glutamate. After the area of a 480/520 ratio value in a control without treatment of a test drug was set to 100%, an inhibitory effect of the test drug was calculated as a percentage (%) thereon.

For accurate calcium imaging, the light source of 4 xenon lamps in FDSS6000 were radiated to selectively expose the cells to the excitation wavelength (480 nm) by a computer-controlled filter wheel. Data were obtained at intervals of 1.23 sec. The emitter fluorescence light inflowed through a 520 nm long-pass filter was obtained as an average 480/520 ratio value for each well in the 96-wells by using a CCD camera and a digital fluorescence analyzer in FDSS6000. All image data and analyses were obtained by using a FDSS6000-exclusive program from Hamamatsu Photonics. The results are shown in Table 1.

TABLE 1

| | % Inhibition rate (mGluR5) | |
|---|---|---|
| Compound | 10 µM | 1 µM |
| Example 11 | 67.71 | 35.88 |
| Example 12 | 64.31 | 31.02 |
| Example 13 | 16.43 | 9.49 |
| Example 14 | 68.03 | 63.58 |

TABLE 1-continued

| Compound | % Inhibition rate (mGluR5) | |
|---|---|---|
| | 10 μM | 1 μM |
| Example 15 | 23.77 | 24.03 |
| Example 16 | 24.32 | 18.01 |
| Example 17 | 8.02 | 11.72 |
| Example 18 | 20.67 | 21.09 |
| Example 19 | 65.78 | 43.93 |
| Example 20 | 67.72 | 67.68 |
| Example 21 | 66.63 | 47.16 |
| Example 22 | 28.5 | 10.56 |
| Example 23 | 17.58 | 25.22 |
| Example 24 | 28.35 | 11.16 |
| Example 25 | 40.07 | 22.02 |
| Example 26 | 76.66 | 58.81 |
| Example 27 | 62.44 | 17.12 |
| Example 28 | 22.15 | 17.36 |
| Example 29 | 77.52 | 56.73 |
| Example 30 | 55.24 | 31.31 |
| Example 31 | 40.09 | 18.85 |
| Example 32 | 58.04 | 23.26 |
| Example 33 | 76.09 | 35.22 |
| Example 34 | 66.48 | 21.89 |

TABLE 1-continued

| Compound | % Inhibition rate (mGluR5) | |
|---|---|---|
| | 10 μM | 1 μM |
| Example 35 | 50.66 | 12.99 |
| Example 36 | 63.29 | 33.87 |
| Example 37 | 66.27 | 29.00 |
| Example 38 | 28.66 | 15.77 |
| Example 39 | 64.82 | 32.96 |
| Example 40 | 46.90 | 29.59 |
| Example 41 | 48.62 | 16.60 |
| Example 42 | 28.63 | 17.08 |
| Example 43 | 15.87 | 17.34 |
| Example 44 | 15.59 | 15.96 |
| Example 45 | 22.45 | 13.60 |

Experimental Example 2

Assays for Inhibitory Concentration ($IC_{50}$) on mGluR5 and hERG, HLM Stability and CYP Inhibitory Rate Several compounds having relatively high inhibitory activity were selected from the results of Table 1 and subjected to assays for measuring $IC_{50}$ (mGluR5 and hERG), HLM (human liver microsomal) stability, and CYP inhibitory rate. The results are shown in Table 2.

TABLE 2

| Compound | mGluR5 $IC_{50}$ (μM) | hERG $IC_{50}$ (μM) | HLM % remaining after 30 min | CYP (% remaining @ 10 μM) | | |
|---|---|---|---|---|---|---|
| | | | | CYP2D6 | CYP2C9 | CYP3A4 |
| Example 14 | 0.41 ± 0.07 | 61.70 ± 11.20 | <1 | >99 | 55 | 50 |
| Example 20 | 0.43 ± 0.02 | 65.30 ± 17.70 | <1 | 86 | >99 | 29 |
| Example 26 | 0.94 ± 0.25 | 20.30 ± 6.11 | 88 | 98 | >99 | 77 |
| Example 39 | 0.75 ± 0.17 | 22.70 ± 7.04 | 98 | 78 | 52 | 56 |

As can be seen in Table 2, it was found that the compound prepared in Example 26 showed a high $IC_{50}$ value for mGluR5 while having a low $IC_{50}$ value for hERG, and exhibited excellent HLM stability and CYP inhibitory effect.

Experimental Example 3

Pharmacokinetic Parameters

After the compound prepared in Example 26 was intravenously injected (n=4) or orally administered (n=3) to rat plasma models, their pharmacokinetic parameters were compared. The results are shown in Table 3.

TABLE 3

|  | Intravenous injection | Oral administration |
|---|---|---|
| $C_{max}$ (μg/mL) | — | 0.43 (±0.18) |
| $T_{max}$ (min) | — | 10 (5-30)[a] |
| $T_{1/2}$ (min) | 58.24 (±62.41) | 48.53 (±8.06) |
| CL (mL/min/kg) | 84.93 (±8.98) | — |
| $V_{dss}$ (mL/kg) | 1269.02 (±158.55) | — |
| B/P ratio, at 2 h | 0.08 | 0.35 |
| F (%) | — | 15.9% |

$C_{max}$: Plasma concentration
$T_{max}$: Time to reach $C_{max}$
$V_{dss}$: Volume of distribution at steady-state
F: Biological utility
[a]Median value for $T_{max}$ As shown in Table 3, it was confirmed that the compound prepared in Example 26 exhibited excellent pharmacokinetics that complied with its in vitro experimental data illustrated in Table 2.

Experimental Example 4

In Vivo Test in Neuropathic Pain Models

The compound prepared in Example 26 was subjected to an in vivo test as follows. Briefly, after the compound of Example 26 was orally administered to SNL (spinal nerve ligation) neuropathic pain models (*Pain* 1992, 55, 85), inhibitory effects thereof on mechanical and cold allodynia were examined. Here, gabapentin was used as a control. The results are shown in FIG. 1.

A) and B) of FIG. 1 represent the inhibitory effects on mechanical allodynia, and C) and D) thereof represent the inhibitory effects on cold allodynia. *P<0.05 (gabapentin), #P<0.05 (Compound of Example 26) vs pre-administration value (paired t-test), ♣ P<0.05 gabapentin vs Compound of Example 26 (unpaired t-test).

As can be seen in FIG. 1, it was found that comparing with gabapentin as a control, the compound of Example 26 showed similar inhibitory effect on mechanical allodynia to that of gabapentin and higher inhibitory effect on cold allodynia than that thereof.

The invention has been described in detail with reference to exemplary embodiments thereof. However, it will be appreciated by those skilled in the art that changes may be made in these embodiments without departing from the principles and spirit of the invention, the scope of which is defined in the appended claims and their equivalents.

What is claimed is:

1. A compound selected from the group consisting of 2-(substituted ethynyl)quinoline derivatives represented by the following Formula 1 and pharmaceutically acceptable salts thereof:

[Formula 1]

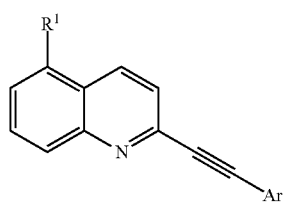

wherein Ar is an heteroaryl group comprising pyrimidinyl, wherein the heteroaryl group being unsubstituted or substituted with one to three substituents selected from the group consisting of halo, cyano, $C_1$-$C_{10}$ alkyl, and $C_1$-$C_{10}$ alkoxy; or Ar is a pyridinyl being substituted with one to three substituents selected from the group comprising halo, cyano, $C_1$-$C_{10}$ alkyl, and $C_1$-$C_{10}$ alkoxy; or Ar is an unsubstituted pyridinyl having N portion in the 3rd position; and $R^1$ is a hydrogen atom, a halogen atom, a hydroxyl group, $C_1$-$C_{10}$ alkyl, $C_1$-$C_{10}$ alkoxy, or $C_1$-$C_{10}$ alkyl carbonate.

2. The compound according to claim 1, which is selected from the group consisting of:
2-(pyridine-3-ylethynyl)quinoline;
5-methoxy-2-(pyridine-3-ylethynyl)quinoline;
5-ethoxy-2-(pyridine-3-ylethynyl)quinoline;
2-(pyridine-3-ylethynyl)quinoline-5-ylpivalate;
2-(pyridine-3-ylethynyl)quinoline-5-ol;
5-chloro-2-(pyridine-3-ylethynyl)quinoline;
5-bromo-2-(pyridine-3-ylethynyl)quinoline;
2-(pyridine-2-ylethynyl)quinoline-5-ylpivalate;
2-(pyridine-2-ylethynyl)quinoline-5-ol;
5-chloro-2-(pyridine-2-ylethynyl)quinoline;
5-bromo-2-(pyridine-2-ylethynyl)quinoline;
2-((3-fluoropyridine-2-yl)ethynyl)quinoline;
2-((3-methylpyridine-2-yl)ethynyl)quinoline;
2-(quinoline-2-ylethynyl)isonicotinonitrile;
2-((4-methylpyridine-2-yl)ethynyl)quinoline;
2-((5-fluoropyridine-2-yl)ethynyl)quinoline;
2-((5-methylpyridine-2-yl)ethynyl)quinoline;
6-(quinoline-2-ylethynyl)picolinonitrile;
2-((6-fluoropyridine-2-yl)ethynyl)quinoline;
2-((6-methoxypyridine-2-yl)ethynyl)quinoline;
2-(pyrimidine-2-ylethynyl)quinoline;
2-((5-fluoropyrimidine-2-yl)ethynyl)quinoline; and
2-(pyrimidine-5-ylethynyl)quinoline.

3. A pharmaceutical composition for treating mGluR5 receptor-mediated diseases, which comprises a compound selected from the group consisting of 2-(substituted ethynyl)quinoline derivatives represented by the following Formula 1 and pharmaceutically acceptable salts thereof as an active ingredient

[Formula 1]

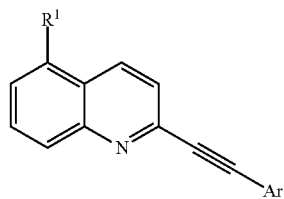

wherein Ar is an aryl or a heteroaryl group selected from the group comprised of phenyl and pyrimidinyl, wherein the aryl or heteroaryl group being unsubstituted or substituted with one to three substituents selected from the group consisting of halo, cyano, $C_1$-$C_{10}$ alkyl, and $C_1$-$C_{10}$ alkoxy; or Ar is a pyridinyl being substituted with one to three substituents selected from the group comprised of halo, cyano, $C_1$-$C_{10}$ alkyl, and $C_1$-$C_{10}$ alkoxy; or Ar is an unsubstituted pyridinyl having N portion in the 3rd position; and $R^1$ is a hydrogen atom, a halogen atom, a hydroxyl group, $C_1$-$C_{10}$ alkyl, $C_1$-$C_{10}$ alkoxy, or $C_1$-$C_{10}$ alkyl carbonate, wherein the mGluR5 receptor-mediated disease is selected from the group consisting of Alzheimer's disease, senile dementia, Parkinson's disease, L-DOPA-induced dyskinesia, Huntington's chorea, amyotrophic lateral sclerosis, multiple sclerosis, schizophrenia, anxiety disorder, depression, neuropathic pain, drug dependence, fragile X syndrome, autism, migraine and gastroesophageal reflux disease (GERD).

4. The pharmaceutical composition according to claim 3, wherein the active ingredient is selected from the group consisting of:
2-(phenylethynyl)quinoline;
5-methoxy-2-(phenylethynyl)quinoline;
2-(phenylethynyl)quinoline-5-ylpivalate;
2-(phenylethynyl)quinoline-5-ol;
5-chloro-2-(phenylethynyl)quinoline;
5-bromo-2-(phenylethynyl)quinoline;
2-(pyridine-3-ylethynyl)quinoline;
5-methoxy-2-(pyridine-3-ylethynyl)quinoline;
5-ethoxy-2-(pyridine-3-ylethynyl)quinoline;
2-(pyridine-3-ylethynyl)quinoline-5-ylpivalate;
2-(pyridine-3-ylethynyl)quinoline-5-ol;
5-chloro-2-(pyridine-3-ylethynyl)quinoline;
5-bromo-2-(pyridine-3-ylethynyl)quinoline;
2-(pyridine-2-ylethynyl)quinoline-5-ylpivalate;
2-(pyridine-2-ylethynyl)quinoline-5-ol;
5-chloro-2-(pyridine-2-ylethynyl)quinoline;
5-bromo-2-(pyridine-2-ylethynyl)quinoline;
2-((3-fluoropyridine-2-yl)ethynyl)quinoline;
2-((3-methylpyridine-2-yl)ethynyl)quinoline;
2-(quinoline-2-ylethynyl)isonicotinonitrile;
2-((4-methylpyridine-2-yl)ethynyl)quinoline;
2-((5-fluoropyridine-2-yl)ethynyl)quinoline;
2-((5-methylpyridine-2-yl)ethynyl)quinoline;
6-(quinoline-2-ylethynyl)picolinonitrile;
2-((6-fluoropyridine-2-yl)ethynyl)quinoline;
2-((6-methoxypyridine-2-yl)ethynyl)quinoline;
2-(pyrimidine-2-ylethynyl)quinoline;
2-((5-fluoropyrimidine-2-yl)ethynyl)quinoline; and
2-(pyrimidine-5-ylethynyl)quinoline.

* * * * *